US010987361B2

(12) United States Patent
Du et al.

(10) Patent No.: US 10,987,361 B2
(45) Date of Patent: *Apr. 27, 2021

(54) TREATING AUTO-IMMUNE AND AUTO-INFLAMMATORY DISEASES (71) Applicant: Shenzhen Evergreen Therapeutics Co., Ltd., Shenzhen (CN)

(72) Inventors: Tao Tom Du, North Potomac, MD (US); Chang Lee, Bethesda, MD (US)

(73) Assignee: Shenzhen Evergreen Therapeutics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,680

(22) Filed: Sep. 21, 2015

(65) Prior Publication Data

US 2016/0045517 A1 Feb. 18, 2016

Related U.S. Application Data (63) Continuation-in-part of application No. 13/174,939, filed on Jul. 1, 2011, now abandoned, which is a continuation-in-part of application No. 13/021,950, filed on Feb. 7, 2011, now Pat. No. 10,231,976.

(60) Provisional application No. 62/195,649, filed on Jul. 22, 2015, provisional application No. 61/302,325, filed on Feb. 8, 2010.

(51) Int. Cl.
A61K 31/573 (2006.01)
A61K 9/00 (2006.01)
A61K 31/58 (2006.01)
A61K 31/57 (2006.01)
A61K 31/56 (2006.01)

(52) U.S. Cl.
CPC .......... *A61K 31/573* (2013.01); *A61K 9/0075* (2013.01); *A61K 9/0078* (2013.01); *A61K 31/56* (2013.01); *A61K 31/57* (2013.01); *A61K 31/58* (2013.01)

(58) Field of Classification Search
CPC ..................................................... A61K 31/57
See application file for complete search history.

(56) References Cited

U.S. PATENT DOCUMENTS

| | | |
|---|---|---|
| 2001/0033870 A1 | 10/2001 | Luo et al. |
| 2002/0173669 A1 | 11/2002 | Schultz et al. |
| 2004/0162274 A1 | 8/2004 | Paust et al. |
| 2004/0234610 A1 * | 11/2004 | Hall .......... A61M 11/06 424/489 |
| 2005/0042268 A1 | 2/2005 | Aschkenasy et al. |
| 2006/0052306 A1 | 3/2006 | Costantino et al. |
| 2006/0182691 A1 | 8/2006 | Besse et al. |
| 2006/0275360 A1 | 12/2006 | Ahmed et al. |
| 2007/0020197 A1 | 1/2007 | Galli et al. |
| 2007/0178166 A1 | 8/2007 | Bernstein et al. |
| 2008/0269178 A1 | 10/2008 | Miller et al. |
| 2009/0035375 A1 | 2/2009 | Skrtic et al. |
| 2009/0221544 A1 | 9/2009 | Stein et al. |
| 2010/0316724 A1 * | 12/2010 | Whitfield .......... A61K 9/0075 424/489 |
| 2011/0195031 A1 * | 8/2011 | Du .......... A61K 31/56 424/43 |
| 2011/0262502 A1 | 10/2011 | Lee et al. |
| 2013/0029957 A1 | 1/2013 | Giliyar et al. |
| 2013/0203717 A1 | 8/2013 | Gil et al. |
| 2013/0303502 A1 | 11/2013 | Cavanagh et al. |
| 2016/0045517 A1 | 2/2016 | Du et al. |

FOREIGN PATENT DOCUMENTS

| | | |
|---|---|---|
| EP | 2 050 437 A1 | 4/2009 |
| WO | WO-2006/138518 A1 | 12/2006 |
| WO | PCT/US11/23917 | 12/2011 |

OTHER PUBLICATIONS

Tan et al. (IL-17 In Lung Disease: Friend or Foe?).*
Baynon et al. Severe Premenstrual Exacerbaton of Asthma: Effect of Intramuscular Progesterone 1988.*
Tan et al. IL-17 In Lung Disease: Friend or Foe? 2013.*
Ito et al. Mode of Glucocorticoid Actions in Airway Disease. 2006.*
Morishima et al. (Th17-Associated Cytokines as a Therapeutic Target for Steroid-Insensitive Asthma). Dec. 2013.*
Office Action issued in related U.S. Appl. No. 13/021,950 dated Aug. 12, 2016 (26 pages).

(Continued)

*Primary Examiner* — Sarah Alawadi
(74) *Attorney, Agent, or Firm* — Foley & Lardner LLP (57) ABSTRACT

The present invention relates to the formulations, methods and kits for reducing cytokine interleukin-17 (IL-17 or IL-17A) levels in both broncheoalveolar lavage fluid (BALF) and blood/serum and/or for the inhibition of p38 mitogen activating protein kinase (MAPK) activity involving the use of 17α-hydroxyprogesterone caproate (17-OHPC) or derivatives thereof. The formulation may be in the form of an inhalant containing effective amounts of 17-OHPC, and the formulation may be used in a method to treat IL-17 cytokine and/or p38 MAPK mediated autoimmune and auto-inflammatory diseases. Such diseases may include glucocorticoid (GC) insensitive related diseases or conditions. In alternate embodiment, the formulation may include the combined use of budesonide (BUD) with 17-OPHC.

10 Claims, 6 Drawing Sheets

(56) References Cited

OTHER PUBLICATIONS

Eugynon 30 review [downloaded from the website <https://web.archive.org/web/20080421032737/http://www.ciao.co.uk/Eugynon_30_Review_5404407> on Aug. 1, 2016].
Patient Group Direction for Microgynon 30 [downloaded from the website <http://www.nes.scot.nhs.uk/media1422760/pgd_microgynon_30_dec_06.pdf> on Aug. 1, 2016].
Office Action dated Jan. 17, 2017, by the U.S. Patent and Trademark Office in related U.S. Appl. No. 14/860,578 (30 pages).
Office Action dated Feb. 7, 2017, issued by the U.S. Patent and Trademark Office in related U.S. Appl. No. 13/021,950 (25 pages).
Mittelstadt, Paul R., et al "T Cell Receptor-mediated Activation of p38 by Mono-phosphorylation of the Activation Loop Results in Altered Substrate Specificity." The Journal of Biological Chemistry 284:23, pp. 15469-15474, Jun. 5, 2009.Web.
Bhavsar, P., et al. "Relative corticosteroid insensitivity of alveolar macrophages in severe asthma compared with non-severe asthma". Thorax. Sep. 2008; 63(9):784-9.
Irusen, Elvis, et al. "p38 Mitogen-activated protein kinase-induced glucocorticoid receptor phosphorylation reduces its activity: Role in steroid-insensitive asthma." J Allergy Clin Immunol. 109:4. 649-57. Apr. 2002. Web.
Roussel, Lucie, et al. "IL-17 Promotes p38 MAPK-Dependent Endothelial Activation Enhancing Neutrophil Recruitment to Sites of Inflammation." The Journal of Immunology. 184:4531-4537. Apr. 15, 2010. Web.
Barnes, Peter J. "Mechanisms and resistance in glucocorticoid control of inflammation" J Steroid Biochem Mal Biol. May 31, 2010;120(2-3):76-85.
Garfield, Robert L., et al. "Use of progesterone and progestin analogs for inhibition of preterm birth and other uterine contractility disorders." FVV in ObGyn, 2012, 4 (4): 237-244.
Schindler Adolf E., et al. "Classification and pharmacology of progestins." Dec. 10, 2003;46 Suppl 1:S7-S16.
Caritis, Steve N., et al. "Pharmacokinetics of 17-hydroxyprogesterone caproate in multifetal gestation." Am J Obstet Gynecol. Jul. 2011 ; 205(1): 40.e.
Attardi, B.J., et al., Am J Obstet Gynecol. Dec. 2007; 197(6): 599.e1-599.e7.
Romero, Roberto, et al. "Progesterone is not the same as 17-hydroxyprogesterone caproate: implications for obstetrical practice." American Journal of Obstetrics & Gynecology p. 421. Jun. 2013.
Dalton, K. Progesterone or progestogens? British Medical Journal p. 1257. Nov. 20, 1976.
Ruddock, Nicole K., et al. "Progesterone, but not 17-alpha-hydroxyprogesterone caproate, inhibits human myometrial contractions." American Journal of Obstetrics & Gynecology 391.e1. Oct. 2008.
Kuon, Ruben J., et al. "Pharmacological actions of progestins to inhibit cervical ripening and prevent delivery depend upon their properties, the route of administration and the vehicle." American Journal of Obstetrics and Gynecology. May 2010; 202(5): 455.e1-455.e9.
Patel, Yesha, et al. "Hydroxyprogesterone Caproate Injection (Makena) One Year Later to Compound or Not to Compound—That Is the Question." P&T® vol. 37 No. 7, p. 405, Jul. 2012.
Nold, Christopher, et al. "Prevention of preterm birth by progestational agents: what are the molecular mechanisms?" American Journal of Obstetrics and Gynecology. Mar. 2013; 208(3): 223.e1-223.e7.
Vlahos, Ross, et al. "Recent advances in pre-clinical mouse models of COPD." Clinical Science (Lond) 126, 253-265. Feb. 2014.
Janssens J.P., et al. "Physiological changes in respiratory function associated with ageing." European Respiratory Journal. 1999; 13:197-205.
Pinart, Mariona, et al. "IL-17A Modulates Oxidant Stress-Induced Airway Hyperresponsiveness but Not Emphysema.". PLOSone 2013, 8 (3): 1-8.

Hueber, Wolfgang et al. "Effects of AIN457, a Fully Human Antibody to Interleukin-17A, on Psoriasis, Rheumatoid Arthritis, and Uveitis." Science Translational Medicine. 2010;2(52):52ra72.
Food and Drug Administration. "FDA approves new psoriasis drug Cosentyx" Jan. 21, 2015. Web.
Stirling, R.G., et. al. "Severe asthma: definition and mechanisms". Allergy 2001:56:825-840.
Rathore, Asmita M. et al. Hormones in Obstetrics and Gynaecology. 2015 Jaypee Brothers Publishers.
Scott-Moncrieff, J.C. et al. "Serum disposition of exogenous progesterone after intramuscular administration in bitches." American Journal of Veterinary Research. Jun. 1990;51(6):893-5.
Keenan, Christine R., et al. "Heterogeneity in Mechanisms Influencing Glucocorticoid Sensitivity: The Need for a Systems Biology Approach to Treatment of Glucocorticoid-resistant Inflammation." Pharmacology & Therapeutics 150 (2015): 81-93. Web.
Chrousos, George P. "Hyperaldosteronism Differential Diagnoses." Hyperaldosteronism Differential Diagnoses. Medscape, Oct. 14, 2014. Web.
Yang, Nan, et al. "Current Concepts in Glucocorticoid Resistance." Current Concepts in Glucocorticoid Resistance. Elsevier, Jun. 20, 2012. Web.
Vazquez-Tello, et al. "Glucocorticoid Receptor-Beta Up-Regulation and Steroid Resistance Induction by IL-17 and IL-23 Cytokine Stimulation in Peripheral Mononuclear Cells." National Center for Biotechnology Information. U.S. National Library of Medicine, Nov. 16, 2012. Web.
Zijlstra, G.J. et al. "Interleukin-17A induces glucocorticoid insensitivity in human bronchial epithelial cells." European Respiratory Journal. Feb. 2012. Web.
Leung D.Y.M., et al. J Exp Med. Nov. 3, 1997; 186(9): 1567-157. Web.
Jin Wei, et al. "IL-17 cytokines in immunity and inflammation" Emerging Microbes and Infections. Sep. 2013. Web.
Park, Heon, et al. "A distinct lineage of CD4 T cells regulates tissue inflammation byproducing interleukin 17." Nat Immunol. Nov. 2005 ; 6(11): 1133-1141. Web.
Konya Christine, et al. "Update on the role of Interleukin 17 in rheumatologic autoimmune diseases." ScienceDirect. Jan. 9, 2015. Web.
Allen, Judith E., et al. "IL-17 and neutrophils: unexpected players in the type 2 immune response." Current Opinion in Immunology 2015, 34:99-106. Web.
Kudo, Makoto, et al. "IL-17A produced by $\alpha\beta$ T cells drives airway hyper-responsiveness in mice and enhances mouse and human airway smooth muscle contraction." Nature Medicine Nat Med 18.4 (2012): 547-54. Web.
Vroman, Heleen, et al. "Mode of Dendritic Cell Activation: The Decisive Hand in Th2/Th17 Cell Differentiation. Implications in Asthma Severity?" Immunobiology 220.2 (2015): 254-61. Web.
Caramori, Gaetano, et al. "Cytokine Inhibition in the Treatment of COPD." International Journal of Chronic Obstructive Pulmonary Disease COPD (2014): 397. Web.
Kang, Min-Jong, et al. "IL-18 Induces Emphysema and Airway and Vascular Remodeling via IFN-g, IL-17A, and IL-13." American Journal of Respiratory and Critical Care Medicine, Jun. 1, 2012. Web.
Suzuki, Hidemi, et al. "Role of Complement Activation in Obliterative Bronchiolitis Post-Lung Transplantation." The Journal of Immunology, Jul. 12, 2015. Web.
Morishima, Yuko, et al. "Th17-Associated Cytokines as a Therapeutic Target for Steroid-Insensitive Asthma." Clinical and Developmental Immunology. vol. 2013, Article ID 609395, 9 pages. Dec. 5, 2013. Web.
Busse, William W., et al. "Randomized, Double-Blind, Placebo-controlled Study of Brodalumab, a Human Anti-IL-17 Receptor Monoclonal Antibody, in Moderate to Severe Asthma." American Journal Respiratory and Critical Care Medicine vol. 188, Iss. 11, pp. 1294-1302, Dec. 1, 2013.
Amara, Suneetha, et al. "Synergistic effect of pro-inflammatory TNF and IL-17 in periostin mediated collagen deposition: Potential role in liver fibrosis." Molecular Immunology 64.1 (2015): 26-35. Web.

(56) References Cited

OTHER PUBLICATIONS

Qiao, Guilin, et al. "A77 1726, the active metabolite of leflunomide, attenuates lupus nephritis by promoting the development of regulatory T cells and inhibiting IL-17-producing doublenegative T cells." Clinical Immunology 157.2 (2015): 166-74. Web.
Honkanen, Jarno, et al. "IL-17 Immunity in Human Type 1 Diabetes." The Journal of Immunology 185.3 (2010): 1959-967. Web.
Vasanthakumar, Rathinam, et al. "Serum IL-9, IL-17, and TGF-b levels in subjects with diabetic kidney disease (CURES-134)." Cytokine 72.1: 109-12. Dec. 23, 2014. Web.
Kim, Yang-Gyun, et al. "Gene Polymorphisms of Interleukin-17 and Interleukin-17 Receptor Are Associated with End-Stage Kidney Disease." American Journal of Nephrology. 2012;36:472-477. Nov. 7, 2012.
Emamauille, Juliet A., et al. "Inhibition of Th17 Cells Regulates Autoimmune Diabetes in NOD Mice." Diabetes Journals. vol. 58. Jun. 2009.
Knier, Benjamin, et al. "Neutralizing IL-17 protects the optic nerve from autoimmune pathology and prevents retinal nerve fiber layer atrophy during experimental autoimmune encephalomyelitis." Journal of Autoimmunity. 56:34-44. Oct. 1, 2014. Web.
Cornelius, Denise C., et al. "Abstracts / Pregnancy Hypertension: An International Journal of Women's Cardiovascular Health 5 (2015) 2-52." Oct. 2014. Web.
Kissi, Yousri EL, el at. "IncreasedInterleukin-17and decreased BAFF serum levels in drug-free acute schizophrenia." Psychiatry Research. 225 (1-2):58-63. Oct. 14, 2014. Web.
Seow C.H., et al., Gas. 2015, 148 (4), S1 454-455 [00022] It has also been shown that.
Boardman, C., et al. "Mechanisms of glucocorticoid action and insensitivity in airways disease." Pulmonary Pharmacology & Therapeutics. 29:129-43. 2014. Web.
Newcomb, Dawn C., et al. Journal of Clinical Immunology. pii: S0091-6749(15)00840-4. Aug. 1, 2015. Web.
Aujla, Shean J. et al. "IL-22 mediates mucosal host defense against Gram-negative bacterial pneumonia." Nature Medicine. Mar. 2008; 14(3):275-281.
Saijo, Shinobu et al. "Dectin-2 Recognition of a-Mannans and Induction of Th17 Cell Differentiation Is Essential for Host Defense against Candida albicans." Immunity. 2010 32(5):681-91. May 2010. Web.
Milner, Joshua D., et al. "Impaired TH17 cell differentiation in subjects with autosomal dominant hyper-IgE syndrome." Nature. 452: 773-776. Apr. 10, 2008. Web.
Francois, Antoine et al. "B cell activating factor is central to bleomycin- and IL-17-mediated experimental pulmonary fibrosis." Journal of Autoimmunity. 56: 1-11. Oct. 23, 2014. Web.
Martinu, T. et al. "IL-17 mediates post-transplant airways and parenchymal lung fibrosis." The Journal of Heart and Lung Transplantation, 34:4, Apr. 2015. Web.
Gong, Fangchen., et al. "The paradoxical role of IL-17 in atherosclerosis." Cellular Immunology. May 29, 2015. Web.
Fujino, S., et al. "Increased expression of interleukin 17 in inflammatory bowel disease." Gut; 52:65-70. 2003. Web.
Hueber, Wolfgang, et al. "Effects of AIN457, a Fully Human Antibody to Interleukin-17A, on Psoriasis, Rheumatoid Arthritis, and Uveitis." Gut; 61(12):1693-700. 2012. Web.
Gold, Ralf, et al. "Interleukin-17—Extended Features of a Key Player in Multiple Sclerosis." The American Journal of Pathology. 172:1, Jan. 2008.
De Pasquale L., et al. "Increased muscle expression of interleukin-17 in Duchenne muscular dystrophy." Neurology. 2012; 78:1309-1314. Web.
Potvin, Stephane, et al. "Inflammatory Cytokine Alterations in Schizophrenia: A Systematic Quantitative Review." Society of Biological Psychiatry. 2008;63:801-808. Web.
Roy, Tapash, et al. "Epidemiology of depression and diabetes: A systematic review." Journal of Affective Disorders. 142S1 (2012) S8-S21. Web.
Tsoukas, Alexander, et al. "Targeting the IL-17/IL-23 Axis in Chronic Inflammatory Immune-Mediated Diseases." Molecular Biology of B Cells (2nd Edition), 2015, p. 527-539.
Novartis. Dec. 26, 2014. Web. https://www.novartis.com/news/media-releases/novartis-announces-fda-approval-first-il-17a-antagonist-cosentyxtm-secukinumab.
Mantovanit, Alberto et al. "Cancer related inflammation." Nature. Jul. 24, 2008;454(7203):436-44.
Wu, Dang, et al. "Interleukin-17: A Promoter in Colorectal Cancer Progression." Clinical and Developmental Immunology vol. 2013, Article ID 436307. Web.
He, Donggou, et al. "IL-17 Mediated Inflammation Promotes Tumor Growth and Progression in the Skin." PLoS ONE. 7:2. e32126. Feb. 2012. Web.
Ortiz, Myrna L., et al. "Immature myeloid cells directly contribute to skin tumor development by recruiting IL-17-producing CD4+ T cells." J Exp Med. Mar. 9, 2015;212(3):351-67.
Oshiro Kiyotetsu et al. "Interleukin-17A is involved in enhancement of tumor progression in murine intestine." Immunobiology. 2012;217(1):54-60.
Chung, Kian Fan. "p38 Mitogen-Activated Protein Kinase Pathways in Asthma and COPD." CHEST 2011; 139(6): 1470-1479.
Coulthard, Lydia R., et al. "p38MAPK: stress responses from molecular mechanisms to therapeutics." Trends Mol Med. Aug. 2009 ; 15(8): 369-379. Web.
Araya-Sibaja, A.M. et al. (2014) "Dissolution properties, solid state transformation and polymorphic crystallization: progesterone case study," Pharm Dev Technol. 19(7):779-788.
Bauer, J.F. (2009) "Pharmaceutical Solids—The Amorphous State," Journal of Validation Technology 15(3):63-68.
Chew, N.Y.K. et al. (2002) "Effect of Powder Polydispersity on Aerosol Generation," J Pharm Pharmaceut Sci. 5(2):162-168.
Chikhalia, V. et al. (2006) "The effect of crystal morphology and mill type on milling induced crystal disorder," European Journal of Pharmaceutical Sciences 27(1):19-26.
Creed, T.J. et al. (2009) "The Effects of Cytokines on Suppression of Lymphocyte Proliferation by Dexamethasone," J Immunol 183:164-171.
Djupesland, P.G. (2013) "Nasal drug delivery devices: characteristics and performance in a clinical perspective—a review," Drug Deliv and Transl Res. 3(1):42-62.
Dvorsky, R. et al. (2011) "Dynamics analysis of cavitation disintegration of microparticles during nanopowder preparation in a new Water Jet Mill (WJM) device," Advanced Powder Technology 22:639-643.
Ettmeyer, P. et al. (2004) "Lessons Learned from Marketed and Investigational Prodrugs," J. Medicinal Chem. 47(10):2393-2404.
Falchetti, R. et al. (1998) "Determination of cytokine co-expression in individual splenic CD4 and CD8 T cells from influenze virus-immune mice," Immunology 95:346-351.
Final Office Action in U.S. Appl. No. 13/021,950, dated May 6, 2015.
Final Office Action in U.S. Appl. No. 13/021,950, dated Oct. 22, 2013.
Final Office Action in U.S. Appl. No. 14/860,578, dated Jul. 25, 2017.
Final Office Action U.S. Appl. No. 13/021,950, dated Apr. 2, 2018.
Gil, M. et al. (2010) "Scale-up methodology for pharmaceutical spray drying," Chemistry Today 28(4):18-22.
Guthrie, G.P. et al. (1980) "The in Vivo Glucocorticoid and Antiglucocorticoid Actions of Medroxyprogesterone Acetate," Endocrinology 107(5):1393-1396.
International Search Report in International Application No. PCT/US2011/023917, dated Oct. 25, 2011.
Junghanns, J-U.A.H. et al. (2008) "Nanocrystal Technology, Drug Delivery and Clinical Applications," International Journal of Nanomedicine 3(3):295-310.
Junyaprasert, V.B. et al. (2015) "Nanocrystals for enhancement of oral bioavailability of poorly water soluble drugs," Asian Journal of Pharmaceutical Sciences 10(1):13-23.
Kam, J.C. et al. (1993) "Combination IL-2 and IL-4 Reduces Glucocorticoid Receptor-Binding Affinity and T Cell Response to Glucocorticoids," J Immunol. 151:3460-3466.

(56) References Cited

OTHER PUBLICATIONS

Keck, C. et al. (2008) "Second generation of drug Nanocrystals for delivery of poorly soluble drugs: smart crystals technology," Dosis. 24(2):124-128.

Khadka, P. et al. (2014) "Pharmaceutical particle technologies: An approach to improve drug solubility, dissolution and bioavailability," Asian Journal of Pharmaceutical Sciences 6:304-316.

Krause, K.P. et al. (2000) "Heavy metal contamination of nanosuspension produced by high pressure homogenization," International Journal of Pharmaceutics 196(2):169-172.

Labiris, N.R. et al. (2003) "Pulmonary drug delivery. Part I: Physiological factors affecting therapeutic effectiveness of aerosolized medications," British Journal Clinical Pharmacology 56(6):588-599.

Larran, J.M. (2005) "Micronisation of pharmaceutical powders for use in inhalation," Pharmaceutical Manufacturing and Packaging Sourcer. Spring 2005.

Lonare, A.A. et al. (2013) "Antisolvent crystallization of poorly water soluble drugs," International Journal of Chemical Engineering and Applications 4(5):337-341.

Macintyre, N.R. (2006) "Corticosteroid Therapy and Chronic Obstructive Pulmonary Disease," Respir Care 51(3):289-296.

Mantovani, G. et al. (1997) "Medroxyprogesterone acetate reduces the in vitro production of cytokines and serotonin involved in anorexia/cachexia and emesis by peripheral blood mononuclear cells of cancer patients," Eur J Cancer 33(4):602-607.

Masterisizer 2000 User Manual. MAN0384 Issue 1.0 Mar. 2007. Malvern Instruments Ltd.

Moschwitzer, J.P. (2013) "Drug Nanocrystals in the commercial pharmaceutical development process," International Journal or Pharmaceutics 453:142-156.

Nakach, M. et al. (2004) "Comparison of various milling technologies for grinding pharmaceuticals," International Journal of Mineral Processing 74:S173-S181.

Nekkanti, V. et al. (2012) "Drug Nanoparticles—An Overview," The Delivery of Nanoparticles:111-132.

Non-Final Office Action in U.S. Appl. No. 13/021,950, dated Apr. 2, 2013.

Non-Final Office Action in U.S. Appl. No. 13/021,950, dated Aug. 27, 2014.

Non-Final Office Action in U.S. Appl. No. 13/021,950, dated Mar. 21, 2016.

Non-Final Office Action in U.S. Appl. No. 13/021,950, dated Sep. 1, 2017.

Non-Final Office Action in U.S. Appl. No. 14/860,578, dated Apr. 6, 2018.

Notice of Allowance U.S. Appl. No. 13/021,950, dated May 1, 2018.

Nunez, B. et al. (2011) "Anti-Tissue Antibodies Are Related to Lung Function in Chronic Obstructive Pulmonary Disease," Am J Respir Crit Care Med. 183(8):1025-1031.

Poulin et al. (1989) Breast Cancer Res Treatment 13:161.

Ringold, H.J. et al. (1956) "Steroids. LXXIII. The Direct Oppenauer Oxidation of Steroidal Formate Esters. A New Synthesis of 17alpha-Hydroxyprogesterone," J Amer Chem Soc 78:816-819.

Saaresranta, T. et al. (2005) "Medroxyprogesterone improves nocturnal breathing in postmenopausal women with chronic obstructive pulmonary disease," Respiratory Res. 6:28.

Sani, S.N. et al. (2009) "Effect of microfluidization parameters on the physical properties of PEG-PLGA nanoparticles prepared using high pressure microfLuidization," Journal of Microencapsulation 26(6):556-561.

Sharma, P.H. et al. (2015) "Poorly Soluble Drugs—A Challenge in Drug Delivery System," European Journal of Pharmaceutical and Medical Research 2(2):484-502.

Shegokar, R. et al. (2010) "Nanocrystals: Industrially feasible multifunctional formulation technology for poorly soluble actives," International Journal of Pharmaceutics 399(1-2):129-139.

Siew, A. (2014) "Pulmonary Drug delivery—Particle Engineering for Inhaled Therapeutics," Pharmaceutical Technology 38(2).

Srivalli, K.M.R. et al. (2014) "Drug Nanocrystals: A way toward scale-up," Saudi Pharmaceutical Journal.

The Merck Index (2001) Table of Progestogens.

Van Rossum, E.F.C. et al. (2011) "Glucocorticoid Resistance," Endocr Dev. 20:127-136.

Vehring, R. (2008) "Pharmaceutical Particle Engineering via Spray Drying," Pharmaceutical Research 25(5):999-1022.

Vippagupta et al. (2001) Advanced Drug Delivery Rev. 48:3-26.

Website Screenshot (2010) (http://www.nlm.nih.gov/medlineplus/immunesystemanddisorders.html).

Yan, R. et al. (2008) "Metabolism of 17alpha-hydroxyprogesterone caproate by hepatic and placental microsomes of human and baboons," Biochem Pharmacol. 75(9):1848-1857.

Beynon, H.L. et al. (1988) "Severe premenstrual exacerbations of asthma: effect of intramuscular progesterone," Lancet 2(8607):370-372.

Final Office Action on U.S. Appl. No. 14/860,578, dated Oct. 17, 2018.

International Search Report and Written Opinion for International Application No. PCT/US2016/052858, dated Dec. 8, 2016, 10 pages.

Loh et al., "Overview of milling techniques for improving the solubility of poorly water-soluble drugs," Asian Journal of Pharmaceutical Sciences, vol. 10, Issue 4, Jul. 2015, 20 pages.

Non-Final Office Action on U.S. Appl. No. 14/860,578 dated Mar. 21, 2019.

Notice of Allowance U.S. Appl. No. 13/021,950, dated Nov. 15, 2018.

Final Office Action on U.S. Appl. No. 14/860,578 dated Oct. 3, 2019.

Newcomb et al., "Estrogen and progesterone decrease Let-7f miRNA expression and increase IL-23/IL-23R signaling and IL-17A production in severe asthma", J Allergy Clin Immunol. Oct. 2015, 163(4), pp. 1025-1034.

Non-Final Office Action on U.S. Appl. No. 14/860,578 dated May 1, 2020, 17 pages.

Final Office Action issued in U.S. Appl. No. 14/860,578 dated Nov. 13, 2020, 11 pages.

\* cited by examiner

TREATING AUTO-IMMUNE AND AUTO-INFLAMMATORY DISEASES

RELATED U.S. APPLICATION DATA

This Continuation-In-Part application claims the benefit of the U.S. patent application Ser. No. 13/174,939 filed on Jul. 1, 2011. The U.S. patent application Ser. No. 13/174,939 is a Continuation-In-Part of application Ser. No. 13/021,950, filed on Feb. 7, 2011, and claims the benefit of PCT International Patent Application No. PCT/US11/23917, filed Feb. 7, 2011, and U.S. Provisional Patent Application No. 61/302,325, filed on Feb. 8, 2010. The entire disclosures of which are incorporated herein by reference. This continuation-in-part application also claims the benefit of U.S. Provisional Patent Application 62/195,649 filed on Jul. 22, 2015. The disclosure of all applications are incorporated by reference in their entirety herein this reference.

FIELD OF THE INVENTION

The present invention relates to the formulations, methods and kits for reducing cytokine interleukin-17 (IL-17 or IL-17A) levels in both broncheoalveolar lavage fluid (BALF) and blood/serum involving the use of 17α-hydroxy-progesterone caproate (17-OHPC). Inhalation of 17-OHPC may treat IL-17 cytokine-mediated auto-immune and auto-inflammatory diseases.

The present invention relates to the formulation, methods and kits in using 17-OHPC in inhibiting phosphorylation (activation) of p38 mitogen-activated protein kinase (MAPK or RK or Cytokinin specific binding protein) in the lungs. Inhalation of 17-OHPC may treat related diseases involving the inhibition of p38 MAPK-mediated phosphorylation.

The present invention relates to the formulations, method and kits involving the inhalation of 17-OHPC in combination with other medicines such as the use of a glucocorticoid (GC), for example, budesonide (BUD). This combinatorial treatment of 17-OHPC and a GC may be used to treat IL-17 cytokine-mediated auto-immune and auto-inflammatory diseases, and with related diseases involving inhibition of p38 MAPK-mediated phosphorylation.

The present invention may be used to reverse GC insensitivity or enhance GC sensitivity in order to treat one or more GC insensitivity related diseases or conditions.

The novel features which are characteristic of the invention, both as to structure and method of operation thereof, together with further objects and advantages thereof, will be understood from the following description, considered in connection with the accompanying drawings, in which the preferred embodiment of the invention is illustrated by way of example. It is to be expressly understood, however, that the drawings or figures are for the purpose of illustration and description only, and they are not intended as a definition of the limits of the invention.

GENERAL BACKGROUND AND STATE OF THE ART

GC signaling mechanisms have "remarkable complexity and contextual dependence" where the mechanism of action of glucocorticoid insensitivity varies amongst different cell types and contexts. Keenan C. R., et al., Pharmacology & Therapeutics 2015, 150:81-93. For example, treatment of inflammation of asthma and chronic obstructive pulmonary diseases (COPD) are distinct as they involve different (although overlapping) cell types and different signaling networks. Id. Such differences gives rise to the different responses to GC treatment where "in most asthmatics, inflammation is well-controlled by inhaled glucocorticoid treatment, whilst the inflammation in COPD is not." Id.

Congenital glucocorticoid resistance is a rare disorder, as described by Dr. George P Chrousos, an internally-known expert in Endocrinology. "Affected patients have an absence of cushingoid features, increased cortisol and ACTH levels (compensating for reduced glucocorticoid receptor function), and resistance to dexamethasone suppression of cortisol levels." Additionally, "treatment [of familial glucocorticoid resistance] consists of high-dose synthetic glucocorticoids with minimal mineralocorticoid activity (e.g., dexamethasone 1-3 mg/day) to suppress plasma levels of ACTH and, ultimately, the secretion of adrenal steroids with androgenic and mineralocorticoid activity." http://emedicine.medscape.com/article/920713-differential.

Regardless of whether the resistance arises from a congenital disorder or not, the high doses of GC required for less responsive patients means a high risk of developing very serious side effects. Yang N., et al., Steroids, 2012, 77(11): 1041-1049.

In Keenan et al., 2015, causes for glucocorticoid receptor (GR) resistance vary by cell, tissue and are organ system specific. With the existence of multiple GR isoforms, "each GR signaling mechanism may occur simultaneously, and either independently or inter-dependently", resulting in broad consequences in cellular function. Id. Furthermore, "one or another molecular action of GR may dominate under different cellular contexts." Id. Meaning, the same cell type may respond differently in various cellular contexts, or even different genes within the same cell may be activated or repressed depending on differential genomic expression. Id.

GR-beta up-regulation by IL-17 and IL-23 cytokines has been demonstrated to induce glucocorticoid resistance in peripheral blood mononuclear blood cells (PMBC) and lead to an inflammatory response. Vazquez-Tello A., et al., J Clin. Immunol. 2013, 33:466-478. IL-17 significantly increases GR-beta expression and is distinguished from IL-2/IL-4 which significantly decreased GR-alpha expression without affecting GR-beta. Id. Furthermore, IL-17 is linked with inducing glucocorticoid insensitivity in human airway epithelium. Zijlstra G. J., et al., Eur Respir J. 2012 February; 39(2):439-45.

Studies revealed that "GC-insensitive asthma results from high level expression of IL-2 and IL-4 which leads to reduced [GR] binding affinity and decreased T cell responsiveness to GCs". Leung D. Y. M., et al., J Exp Med. 1997 Nov. 3; 186(9): 1567-1574. Patients suffering from "GC-insensitive asthma have a reversible defect in PBMC GR ligand binding affinity which can be sustained by the addition of IL-2 and IL-4". Id. A combination treatment of normal peripheral blood T-cells with IL-2 and IL-4 reduces GR ligand binding affinity to a level indicative in glucocorticoid insensitive asthma. Id. Furthermore, glucocorticoid insensitive airway T-cells have significantly higher levels of IL-2 and IL-4 gene expression than glucocorticoid sensitive airway T cells. Id.

IL-17 family and sources. The Interleukin 17 (IL-17) cytokine family contains six members; IL-17A, IL-17B, IL-17C, IL-17D, IL-17E, and IL-17F. Jin W. et al., Emerg Microbes Infect. 2013 September; 2(9):e60. Of these, IL-17A is the best characterized and thus commonly referred to as IL-17. Id. IL-17 cytokines mediate their roles by targeting cell surface receptors designated as IL-17RA, IL-17RB, IL-17RC, IL-17RD, and IL-17RE. These receptors are often heterodimers and share similarity by having IL-17RA as a subunit. IL-17 is mainly expressed by activated CD4+ T cells known as Th17 cells. Park H., et al., Nat Immunol. 2005 November; 6(11):1133-41. Alternatively, IL-17 may be expressed by γδT cells which have been shown to localize at mucosal tissue such as the intestine, skin and lungs. Supra Jin W., et al., IL-17 production may also be produced by T-cell subtype innate Th17 (iTh17) αβT cells which are found in the lamina propria of the intestine, as well as produced by alternative cells involved in the innate immune response such as lymphoid tissue inducer cells, natural killer and natural killer T-cells, macrophages, and Paneth cells. Supra Jin W., et al. The IL-17 receptor (IL-17R) family comprises five receptor subunits, of which IL-17RA is the largest member and is necessary for IL-17-mediated signal transduction. Pinart M., et al., PLOSone 2013, 8 (3): 1-8. IL-17 induces the release of the proinflammatory cytokines and other agents such as CXCL-8 from airway epithelial cells, smooth muscle cells and macrophages, and thereby orchestrates neutrophilic inflammation and release of reactive oxygen species. Id.

IL-17 Role in Immunity.

The IL-17 pathway has recently expanded its role in clinical auto-immune and auto-inflammatory diseases. Konya C., et al., Cytokine, In Press, Accepted 8, January 2015. IL-17 induces neutrophilic airway inflammation. Allen J. E., et al., Current Opinion in Immunology 2015, 34:99-106. IL-17 activates mononuclear phagocytes and recruits neutrophils, and thereby induces epithelial antimicrobial responses which protects against extracellular bacteria and fungi. Id. An example of IL-17 mediated auto-immune disease is when Th17 cytokine secretion activates airway epithelial cells via IL-17 to secrete CXCL8, a chemoattractant for neutrophils, and IL-17 leads to the accumulation of neutrophils which promote lung injury. Supra, Allen J. E. et al.

IL-17 has a role in respiratory smooth muscle by increasing contractility by induction of RhoA in airway smooth muscle cells. Kudo M., et al., Nat. Med. 2012, 4; 18(4):547-54. The resultant hypercontractility leads to airway narrowing. Furthermore, IL-17 will induce airway remodeling by increasing smooth muscle cell hyperplasia and collagen deposition. Vroman H., et al., Immunobiology 2015, 220: 254-261. Diseases associated with reduced airflow to the lungs due to smooth muscle hypercontractility and airway remodeling include COPD, obliterative bronchitis, bronchiectasis, cystic fibrosis, sarcoidosis, eosinophilic granuloma, respiratory bronchiolitis interstitial lung disease, and asthma.

Increased levels of IL-17 have been observed in cases of severe asthma and COPD. Caramori, G. et al. Intl. J. of COPD 2014, 9:397-412. However, emphysema and lung inflammation induced by ozone is not dependent on IL-17. Supra Pinart M., et al. Kang M. J. et al. further exemplifies that airway and vascular remodeling associated with COPD (such as tissue fibrosis in airways and blood vessels) is in response to IL-17 which in turn is induced by IL-18. Kang M. J. et al., Am. J. Respir. Crit. Care. Med. 2012 Jun. 1; 185(11):1205-1217. The stimulation of "vascular alterations and remodeling in COPD [is] a direct consequence of [cigarette smoke] or inflammatory mediators" and "IL-18 is a potent stimulator of vascular remodeling that mediates these response via its ability to induce IL-17A". Id. Thus, IL-17 induces "mucus metaplasia, airway fibrosis, and vascular remodeling"; which are characterized pathologies of COPD. Id.

Chronic lung allograft dysfunction, in particular, obliterative bronchiolitis (OB), is the primary limiting factor of successful lung transplantation. Suzuki H., et al., J Immunol 2013, 191:4431-4439. Data showed that IL-17 down-regulates the complement-regulatory protein (CRP) in airway epithelium which translates to the activation of the complement cascade and subsequent complement activation leading to OB pathogenesis. Id.

IL-17 signaling has been implicated in the development and persistence of asthma indicating that targeted strategies blocking IL-17 receptor signaling may be beneficial in asthma treatment. Morishima Y., et al., Clin. Dev. Immuno). 2013, 609395; 1-9. A large clinical trial was conducted to determine efficacy and safety of brodalumab, a human anti-IL-17 receptor A monoclonal antibody, in subjects with inadequately controlled moderate to severe asthma taking regular inhaled corticosteroids. Busse W. W., et al., Am. J. Respire. Crit. Care Med. 2013, 188 (11): 1294-1302.

IL-17 has also been implicated in other diseases. B cell activating factor is central to bleomycin- and IL-17-mediated experimental pulmonary fibrosis. Francois A., et al., J. of Autoimmun. 2015, 56: 1-11. There is a synergistic effect of pro-inflammatory TNFα and IL-17 in periostin (a pro-fibortic factor) mediated collagen deposition which establishes a potential role in liver fibrosis. Amara S., et al., Mol. Immunol, 2015, 64: 26-35. Recent studies by Qiao et al. have shown that A77 1726, the active metabolite of leflunomide, suppresses IL-17 which produces double negative T cells in lymph nodes through an Akt-dependent mechanism, and thus attenuating the generalized auto-immune features of lupus nephritis. Qiao G. et al. Clin. Immunol. 2015, 157(2): 166-174.

Also, an up-regulation of immunity has been characterized by increased IL-17 secretion and expression in anti-CD3 and anti-CD28 Th17 cells and isolated memory CD4 cells in children with T1 D. Honkanen J., et al., J. Immunol. 2010, 185 (3):1959-67. The study also showed that IL-17 induced an inflammatory and proapototic response mediating a detrimental effect on islet cells in vitro. Id. Furthermore, IL-17 has been linked to complications associated with diabetes such as diabetic kidney disease. Vasanthakumar R., et al., Cytokine 2015, 72(1): 109-112; Kim Y. G., et al., Am. J. Nephrol. 2012, 36:472-477. Inhibiting IL-17 by neutralizing antibodies have reduced islet inflammation and have prevented the development of autoimmune diabetes in 10 week old NOD mice. Emamaullee J. A., et al., Diabetes 2009, 58:1302-1311.

Auto-immune encephalomyelitis is a complex disease associated with multiple sclerosis and exhibits pathological features that include inflammation, demyelination, axonal loss, gliosis, and optic neuritis; inflammation and demyelination of the optic nerve. IL-17 mRNA levels were the highest within the optic nerve when compared to the brain and spinal cord in an experimental auto-immune encephalomyelitis (EAE) model. Knier B., et al., J. Autoim. 2015, 56:34-44. Within the optic nerve, there was an abundance of IL-17 producing CD4(+) T cells committed to the Th17 transcriptional program. Id. Neutralization of IL-17 by anti-IL-17 antibodies proved to completely prevent the deterioration of the retinal nerve fiber layer as well as the inner plexiform layer. Id.

Preeclampsia is also associated with a higher level of IL-17 producing Th17 cells where blocking IL-17 confers a reduction of blood pressure and oxidative stress, and relieves intrauterine growth restriction. Cornelius D. C., et al., Pregnancy Hypertens. 2015, 5 (1): 1. In the pathogenesis of schizophrenia, a significant and consistent increase of IL-17 levels was found in schizophrenic patients when compared to controls, highlighting the role of inflammation in neurological disease. Kissi Y. E., et al., Psychiatry Res., 2015, 225 (1-2):58-63. With regards to irritable bowel disease (IBD), studies showed that IL-17 has an immunomodulatory effect in pregnant women suffering IBD. Seow C. H., et al., Gas. 2015, 148 (4), S1 454-455

It has also been shown that activated p38 MAPK results in GR-alpha phosphorylation, which stops nuclear translocation, leading to steroid resistance. Boardman C., et al., Pulm. Pharmacol. & Ther. 2014, 29:129-43. Individuals with severe asthma have reduced nuclear translocation of GR and reduced glucocorticoid responsive element (GRE) binding in PMBCs after exposure to GCs, which may be explained by GR phosphorylation. Id.

Studies also have shown that ovarian hormones, namely, natural progesterone (P4) increase IL-17 production from Th17 cells through an IL-23R and Let-7f mediated pathway in patients with severe asthma conditions. Newcomb D. C., et al., J Allergy Clin. Immunol. 2015 Aug. 1. pii: 50091-6749(15)00840-4. Thus, P4 has been shown to only exacerbate IL-17 mediated diseases.

IL-17 has a distinctive role in mediating clearance of bacterial and fungal pathogens at epithelial and mucosal barriers. In particular, IL-17 has demonstrated involvement in the innate immune response against bacterial pathogens such as *Staphylococcus aureus, Listeria monocytogenes, Klebsiella pneumoniae, Citrobacer rodentium, Mycobacterium* sp., and fungi such as *Pneumocystis carinii* and *Candida albicans*. Supra Jin W., et al. IL-17 mediates inflammation and pathogen clearance by recruiting innate immune cells such as neutrophils via the induction of pro-inflammatory cytokines and chemokines. For example, IL-17 can "induce the production of proinflammatory cytokines (IL-6, granulocyte colony-stimulating factor and granulocyte-macrophage colony stimulation factor)" and upregulate "several cytokines including chemokine (C-X-C motif) ligand 1 (CKCL1), chemokine (C-C motif) ligand 2 (CCL2), CCL7, CCL20 and matrix metalloproteinase 3 and 13." Supra Jin W. et al.

Furthermore, studies have shown that IL-17 knockout mice (Il17a$^{-/-}$) have a decreased level of pro-inflammatory cytokine and chemokine production. Aujla S. J., et al., Nat. Med. 2008 March; 14(3):275-281. Il17$^{-/-}$ a mice have a "significantly lower amount of G-CSF and CXCL1 in bronchoalveolar lavage (BAL) fluid", as well as a "reduction in IL-6 and CCL3 abundance" when compared to wild type mice. Id. Additionally, Il17a$^{-/-}$ mice are defective in their ability to appropriately respond, and are highly susceptible, to systemic infection by *C. albicans*. Saijo S., et al., Immunity. 2010 32(5):681-91. A higher susceptibility to pathogens such as *Streptococcus pneumoniae, S. aureus*, and *C. albicans* due to IL-17 deficiency is also evident in humans with a defective STAT3 gene. Milner J. D., et al., Nat. 2008; 452: 773-776.

IL-17, Chronic Inflammation, and Autoimmune Diseases.

An unfortunate consequence of IL-17 deregulation may result in an overexpression of cytokines and chemokines leading to an excessive pro-inflammatory response and chronic inflammation. For example, IL-17 has been linked to numerous inflammatory and auto-inflammatory diseases such as autoimmune and type-1 diabetes (Emamaullee J. A., et al., Diabetes 2009, 58:1302-1311, and Kudo et. al., Nat. Med. 2012, 4; 18(4):547-54), end-stage kidney disease (Kim Y. G., et al., Am. J. Nephrol. 2012, 36:472-477), obliterative bronchiolitis post-lung transplant (Suzuki H. et al., J. Immunol. 2013, 191:4431-4439), asthma (Supra Busse W. W., et al.), encephalomyelitis (Supra Knier B. et al.), pulmonary fibrosis (Francois A., et al., J. of Autoimmun. 2015, 56: 1-11), liver fibrosis (Supra Amara S., et al., Mol.), chronic obstructive pulmonary disease (Caramori, G. et al., Intl. J. of COPD 2014, 9:397-412), preeclapsia (Cornelius D. C., et al., Pregnancy Hypertens. 2015, 5 (1): 17), parenchymal lung fibrosis (Martinu T., et al., J. Heart and Lung Transpl., 34:4, 2015, 175-6), atherosclerosis (Gong F., et al., Cellular Immunol., In Press, Accepted Manuscript, Available online 29 May 2015), rheumatoid arthritis (Supra Konya C., et al.), systemic lupus erythematosus (Id.), psoriasis (Id.), lupus nephritis (Qiao G., et al., Clin. Immunol. 2015, 157(2): 166-174), inflammatory bowel disease (Fujino S., et al., Gut 2003; 52:65-70), Crohn's disease (Hueber W., et al., Gut 2012; 61(12):1693-700), multiple sclerosis (Gold R., et al., Am. J. Pathol. 2008; 172(1): 8-10.), Duchenne muscular dystrophy (De Pasquale L., et al., Neurology. 201278(17): 1309-14), and psychiatric disorders such as schizophrenia and depression (Potvin S., et al., Psychiatry 2008; 63(8): 801-8 and Roy T., et al., J Affect Disord. 142 Suppl: S8-21).

IL-17 as a Therapeutic Target for Inflammatory Diseases.

Due to the extensive involvement of IL-17 in chemokine and cytokine regulation and the innate immune response, IL-17 remains a prime drug target aimed to treat a broad variety of pro-inflammatory and autoimmune diseases. For example, humanized monoclonal antibodies against IL-17 such as Secukinumab (IgG1$_K$), Ixekizumab (IgG4), and Broadalumab (IgG2) have been clinically tested for their effectiveness in treating rheumatoid arthritis, Crohn's disease, psoriasis, psoriatic arthritis, and ankylosing spondylitis. Tsoukas A., et al., Molecular Biology of B Cells (2nd Edition), 2015, p. 527-539. Secukinumab was shown to "significantly reduced the disease activity [of psoriasis, rheumatoid arthritis, and non infectious uveitis] compared to the placebo-treated group" by "targeted inhibition of the proinflammatory cytokine IL-17A". Hueber W., et al., Sci. Transl. Med. 2010; 2(52):52ra72. The FDA approval of Secukinumab in early 2015 for the treatment of psoriasis, as well as the drug's concurrent approval in Japan for the treatment of psoriasis and arthritis, further demonstrates the potential and clinical necessity towards the development of IL-17 targeted therapeutics. U.S. Food and Drug Administration. 2015-01-21; Novartis AG. 2014-12-26.

IL-17 as a Therapeutic Target for Cancer.

It is widely accepted that chronic inflammation plays an important and contributing role in cancer initiation and progression. Mantovani A., et al., Nature. 2008 Jul. 24; 454(7203):436-44. Not surprisingly, expression levels of IL-17, a proinflammatory cytokine, have been shown to be "elevated in several human tumors, such as ovarian cancer, cervical cancer, breast cancer, hepatocellular carcinoma, esophageal cancer, gastric cancer, and [colorectal cancer]". Wu D., et al., Clin Dev Immunol. 2013; 2013:436307. Mechanisms delineating IL-17 involvement in tumor progression include suppressing antitumor responses as well as promoting angiogenesis through the induction of angiogenic factors such as PGE1, PGE2, VEGF, CXCL-1, CXCL-5, CXCL-6, CXCL8, MMP-2, and MMP-9 (Id.). Therefore, targeting IL-17, for example, by neutralization, decreasing its expression, or blocking downstream signaling pathways has been pursued as a method of cancer treatment. For example, "IL-17 mediated inflammation is an important mechanism of inflammation mediated promotion of tumor development" and progression in the skin. He D., et al., PLoS One. 2012; 7(2):e32126, IL-17 is required for dimethylbenz[a]anthracene (DMBA) and 12-O-tetradecanoylphorbol-13-acetate (TPA) induced carcinogenesis in the skin. Id. Also, neutralization of IL-17 significantly inhibits the progression of DMBA/TPA induced skin tumors.

Id. Similarly, Ortiz M. L. et al. demonstrated that blocking "IL-17 abrogated the increase of [skin] tumor formation caused by [immature] myeloid cells". Ortiz M. L., et al., J Exp Med. 2015 Mar. 9; 212(3):351-67. Furthermore, IL-17 was shown to be involved in intestinal tumor progression, and anti-IL-17 monoclonal antibody treatments decreased tumor size in the cecum of wild type mice. Oshiro K., et al., Immunobiology. 2012, 217(1):54-60.

Background of p38.

Mitogen-activated protein Kinases (MAPK) are proteins involved in a diverse cellular network of phosphorylation cascades resulting in a variety of cellular responses and signaling stimuli. Their activation may be due to a variety of stresses, "such as inflammatory cytokines, pathogens, growth factors, ultraviolet radiation, osmotic stresses, and various forms of oxidative stresses" and DNA damage. Chung K. F., Chest. 2011; 139(6):1470-9. The p38 family of MAPKs consists of conserved proline-directed serine-threonine MAPKs involved in linking extracellular signals to intracellular regulatory mechanisms. Four isoforms of p38 have been identified; p38α, p38β, p38γ, and p38δ, encoded by the MAPK14, MAPK11, MAPK12, and MAPK13 genes, respectively. Activation of p38 typically occurs in response to inflammatory signals by environmental stresses and cytokines. More specifically, activation of p38 is mediated by upstream MAPK kinases (MKKs) or MAPK kinase kinases (MEKKs) via the dual phosphorylation of a conserved Thr-Gly-Tyr motif, allowing for ATP binding and subsequent phosphotransfer to a downstream target protein. Id. However, p38 may also play a role in cell cycle regulation, induction of cell death, differentiation, and senescence. Coulthard L. R., et al., Trends Mol Med. 2009 August; 15(8): 369-379. P38 has also been shown to autophosphorylate in an MKK-independent mechanism. Mittelstadt P. R., et al., J. Biol. Chem. 2009; 284(23): 15469-15474.

There are numerous downstream kinases which the p38 isoforms activate. For example, p38α and β activate MAPK activated protein kinase (MAPKAPK2/3) as well as a variety of transcription factors, cytoskeletal proteins, translational components, and enzymes. Whereas the γ and δ isozymes have been shown to be more specific towards "targeting transcription factors, such as activating transcription factor-2, extracellular signal regulated-like kinase, and serum response factor accessory protein 1." Supra Chung K. F., et al. Active p38 also induces the recruitment and migration of inflammatory cells such as neutrophils, stem cells, and eosinophils and is proposed to "alter corticoid responsiveness in response to oxidative stress." Id. Also, active p38 levels are increased in "macrophages from patients with severe asthma or COPD and [in] epithelial cells from patients with severe asthma, and could contribute to corticosteroid insensitivity." Id.

p38 Role in Glucocorticoid Response.

p38 has been implicated in playing a role in altering glucocorticoid responsiveness. For example, "alveolar macrophages from patients with severe asthma demonstrate CS insensitivity associated with increased p38 MAPK activation that may result from impaired inducibility of [MAPK phosphatases 1 (MKP-1)]". Bhavsar P., et al., Thorax. 2008 September; 63(9):784-90. p38 may lead to glucocorticoid insensitivity by directly inhibiting phosphorylation of GR, promoting histone H3 phoshorylation, and reducing corticosteroid-induction of MKP-1. Supra Chung K. F., et al. A reduction in glucocorticoid sensitivity by p38 MAPK activation may occur through hyperphosphorylation of NF-κB which leads to a reduced interaction with GR. Id.

p38 plays a consistent role in "several chronic cytokine dependent inflammatory diseases, including rheumatoid arthritis, Crohn's disease, psoriasis, and asthma". Supra Coulthard L. R., et al. In asthma and COPD, glucocorticoid insensitivity is characterized by a "reduced effect of dexamethasone in inhibiting the release of proinflammatory cytokines from monocytes and macrophages". Supra Chung K. F., et al. Irusen E. et al. demonstrated that glucocorticoid insensitivity in PBMCs due to concurrent exposure with both IL-2 and IL-4 may be reversed by inhibiting p38 MAPK with the p38 inhibitor SB203580. Irusen E., et al., J Allergy Clin Immunol. 2002 April; 109(4):649-57. Also, increased levels of active p38 have been shown to promote cardiomyocyte dysfunction resulting in cardiovascular disease, as well as contribute to neurodegenerative diseases such as Alzheimer's disease, Huntington's disease, amyotrophic lateral sclerosis, multiple sclerosis, and Parkinson's disease. Supra Coulthard L. R. et al. Diabetes, and the progression of diseases associated with diabetes such as neuropathy and nephropathy, has also been shown to be linked with increased levels of active p38. Id.

Roussel L. et al. demonstrated that IL-17 increases CXCL8 production by lung microvascular endothelial cells (LMVECs) "via the p38 MAPK pathway". Roussel L., et al. J Immunol. 2010 Apr. 15; 184(8):4531-7.

Therapeutics Targeting p38.

The down regulation, inhibition, or decrease in expression of p38 MAPK by inhibitors may thus "have potential not only as anti-inflammatory agents in their own right but also as agents that restore corticosteroid responsiveness". Supra Irusen E., et al. Unfortunately, p38 MAPK inhibitors such as SB203580, BIRB796, SD282, VX745, SCI0469, SD0006, and SB681323 have been reported to target other non-p38 kinases and proteins which may illicit side effects such as liver toxicity. Supra Chung K F et al. A topical administration of p38 inhibitors to the lungs is desired since it "would allow higher topical concentrations at the side of disease with lesser amounts available for the systemic circulation and, hence, fewer side effects". Supra Irusen E. et al.

There remains a need to treat glucocorticoid insensitivity, in particular asthma and COPD. An objective of the present invention is to provide a method of treating autoinflammatory conditions by inhibition of IL-17 expression and p38 expression.

SUMMARY OF THE INVENTION

The present invention is directed to methods for restoring corticosteroid sensitivity or reversing the glucocorticoid insensitivity or enhancing glucocorticoid sensitivity.

One embodiment of the present invention is directed to administering a pharmaceutical composition comprising a steroid hormone to a subject suffering from glucocorticoid insensitivity related condition or conditions. Glucocorticoid insensitivity related conditions include a range of corticoid resistant diseases and immune inflammatory disorders treated with steroids when the therapy becomes ineffective or intolerant or dependent or unresponsive or refractory to corticosteroids, and combinations thereof.

One embodiment of the present invention is directed to administering a pharmaceutical composition comprising a steroid hormone to a subject suffering from autoimmune autoinflammatory related condition or conditions, autoimmune-autoinflammatory related condition or conditions include a range of disorders where cytokines and chemokines lead to an excessive pro-inflammatory response and chronic inflammation. Excessive pro-inflammatory and chronic inflammation conditions consists of but is not limited to type-1 diabetes, end-stage kidney disease, obliterative bronchiolitis post-lung transplant, asthma, severe asthma, encephalomyelitis, pulmonary fibrosis, liver fibrosis, chronic obstructive pulmonary disease, preeclapsia, parenchymal lung fibrosis, atherosclerosis, rheumatoid arthritis, systemic lupus erythematosus, psoriasis, lupus nephritis, inflammatory bowel disease, Crohn's disease, multiple sclerosis, Duchenne muscular dystrophy, and psychiatric disorders such as schizophrenia and depression.

One embodiment of this invention includes formulations, methods and kits involved in administering 17-OHPC for the treatment of glucocorticoid insensitivity that leads to excessive pro-inflammatory and chronic inflammatory conditions.

Another embodiment of this invention includes formulations, methods and kits involved in administering a combination of 17-OHPC and other medicines, for example Budesonide, for the treatment of glucocorticoid insensitivity that leads to excessive pro-inflammatory and chronic inflammatory conditions.

Another embodiment of this invention includes formulations, methods and kits involved in administering 17-OHPC in inhibiting phosphorylation (activation) of p38 MAPK in the lungs.

Yet another embodiment of this invention includes formulations, methods and kits involved in administering a combination of 17-OHPC and other medicines, for example Budesonide, in inhibiting phosphorylation of p38 MAPK in the lungs.

A preferred embodiment of this invention includes formulations, methods and kits involved in administering 17-OHPC to reduce cytokine IL-17 levels in BALF and blood/serum in order to treat auto-immune and auto-inflammatory diseases.

A preferred embodiment of this invention includes formulations, methods and kits involved in administering 17-OHPC to reduce cytokine IL-17 levels in order to treat asthma, severe asthma, or COPD.

Another preferred embodiment of this invention includes formulations, methods and kits involved in administering a combination of 17-OHPC and other medicines, for example Budesonide, to reduce cytokine IL-17 levels in order to treat auto-immune and auto-inflammatory diseases.

Yet another preferred embodiment of this invention includes formulations, methods and kits involved in administering a combination of 17-OHPC and other medicines, for example Budesonide, to reduce cytokine IL-17 levels in order to treat asthma, severe asthma, or COPD.

It is understood that the embodiments above are provided as representative embodiments of the present invention, and in no way are to be constructed as limiting the scope of the present invention.

DEFINITIONS

As used herein, the term "glucocorticoid insensitivity" is intended to include, but is not limited to, corticosteroid resistance, corticosteroid dependence, corticosteroid refractory responses, corticosteroid intolerance, and other types of corticosteroid ineffectiveness. It has been recognized that several distinct molecular mechanisms contribute to decreased anti-inflammatory effects of glucocorticoids. Different inflammatory diseases may share similar molecular mechanisms, and a single disease may have a heterogeneity of mechanisms.

"Corticosteroid resistance" to the anti-inflammatory effects of corticosteroids is defined as no clinical improvement after treatment with high-dose glucocorticoid.

"Corticosteroid dependence" is defined as a condition that initially responds to corticosteroids but relapses quickly upon drug withdrawal or dose tapering.

"Corticosteroid refractory response" is defined as a condition that does not respond to an adequate induction dose of corticosteroids. It includes relatively or totally refractory responses to glucocorticoid therapy, and often needs to be controlled by add-on treatment.

Other types of "corticosteroid ineffectiveness" includes the need for a very high dose treatment, "difficult to treat" and "do not respond well" or severe cases, and impaired in vitro and in vivo responsiveness.

"Corticosteroid intolerance" is defined as toxicity of the therapy and/or risks for developing corticosteroid-related adverse events such as opportunistic infections and bone loss.

"Glucocorticoid sensitizer" is defined as a pharmaceutical agent and product that has a function in restoring corticosteroid sensitivity, enhancing glucocorticoid sensitivity, reversing the glucocorticoid insensitivity, and protecting against loss of glucocorticoid sensitivity, and used for treating, preventing, or ameliorating one or more of the symptoms of diseases or disorders associated with glucocorticoid insensitivity (e.g., corticosteroid dependent or corticoid resistant or unresponsive or intolerant to corticosteroids). Therapeutic effects of the use of a glucocorticoid sensitizer include any, but are not limited to, steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune functions, easier responses for the subject or patient when steroid administration is tapered or withdrawn, or after prolonged administration of corticosteroids, decreased risks for developing corticosteroid-related adverse events such as opportunistic infections, bone loss, pathologic fracture, diabetes, cataract, and combinations thereof.

As used herein, the term "progesterone" or "P4" refers to the chemical compound with systematic name pregn-4-ene-3,20-dione, Chemical Abstracts Services (CAS) number 57-83-0.

As used herein, the term "17α-hydroxyprogesterone caproate" or "17-OHPC" refers to the chemical compound with systematic name 17-[(1-Oxohexyl)oxy]-pregn-4-ene-3,20-dione, CAS Registry Number 630-56-8.

Unless otherwise noted, the term "Interleukin-17" or "IL-17" as used herein, refers to the cytokine protein "IL-17A". Wherein "IL-17A" refers to the protein of any IL-17A protein sequence known in the art.

As used herein, the term "p38" refers to any of the p38 isoforms known in the art, namely, p38α (MAPK14), p38β (MAPK11), p38γ (MAPK12/ERK6), or p38δ (MAPK13/SAPK4), unless otherwise specifically noted.

As used herein, the term "R-group" refers to any combination of carbon, hydrogen, oxygen, nitrogen, and/or halogen atoms attached to the C-17 position on the cholesterol hydrocarbon ring framework.

As used herein, the term "patient" refers to a human receiving or registered to receive medical care or treatment.

As used herein, the term "severe asthma" or "corticosteroid resistant asthma" or "therapy resistant asthma" refers to asthma symptoms and exacerbations that are unresponsive or respond suboptimally to inhaled or systemic corticosteroids resulting in a reduction in effectiveness of corticosteroids in controlling asthma. As defined by Bhavsar P., et. al., suboptimal response in corticosteroid resistant asthma is "defined as <15% of baseline forced expiatory volume in 1 s ($FEV_1$) after taking prednisolone (30-40 mg/day) over 14 days while demonstrating marked bronchodilator response to inhaled $\beta_2$ agonists" as compared to patients with corticosteroid responsive asthma who demonstrate "a>25% improvement in $FEV_1$ after prednisolone treatment". Supra Bhavsar P., et al. Corticosteroid resistant asthma patients also show "a reduction in suppressive effect of dexamethasone on the proliferative response of or release of neutrophil activating factor from peripheral blood mononuclear cells (PMBCs) has been observed". Id. Also, severe asthamtics have increased levels of active p38 than non-severe asthma patients. Id. Furthermore, "decreased glucocorticoid responsiveness is found in patients with severe asthma and asthmatics who smoke, as well as in all patients with COPD and cystic fibrosis". Barnes P. J., J Steroid Biochem Mol Biol. 2010 May 31; 120(2-3):76-85. Mild intermittent asthma may be controlled by $\beta_2$ agonists alone while moderate to severe asthma may necessitate the use of high-dose inhaled or oral corticosteroids. Stirling R. G., et. al., Allergy 2001: 56:825-840.

As used herein, the term "inhalation" refers to inhaling or breathing as a route of administration of a pharmaceutical composition through respiratory passages, wherein delivery of said pharmaceutical composition may preferably be, for example, via an aerosol spray, a powder mixture, gas, or vapor in a pressurized pack or nebulizer or in an inhaler.

DETAILED DESCRIPTION OF THE INVENTION

According to various embodiments, a method of treatment using a pharmaceutical formulation comprising 17-OHPC has shown to be effective in two specific mechanisms: lowering IL-17 levels and inhibiting p38 MAPK activity. Both actions have a therapeutic effect in treating IL-17 and p38 MAPK mediated glucocorticoid resistance. Such a result is surprising given that previous studies using P4 had contrary results.

P4 and 17-OHPC are both classified as progestogen hormones. P4 is a naturally occurring progestogen endogenous to living organisms and may be considered as the chemical equivalent of a genus. P4 is synthesized within the ovaries, testes, placenta, and adrenal gland. Whereas 17-OHPC is a progestin (a synthetic progestogen) derived from 17α-hydroxyprogesterone (17-OHP) and caproic acid.

Structurally, progesterone (molecular weight (MW) of 314.46 g/mol and a melting point of 129.5° C.) and 17-OHPC (MW 428.6 g/mol and a melting point of 119° C.) and progesterone derivatives and metabolites such as, but not limited to, 17-hydroxyprogesteone, 19-norprogesterone, medrogestone, 17-OHPC, hydroxyprogesterone caproate, demegestone, dydrogesterone, medroxyprogesterone acetate, promegestone, megestrol acetate, trimegestone, chlormadinone acetate, gestonorone caproate, cyproterone acetate, nomegestrol, testosterone, 19-nortestosterone, ethisterone, norethisterone, desogestrel, norethylnodrel, norgestimate, tibolone, dienogest, quingestanol, norgestrienone, levo-norgestrel, gestrinone, and gestoden have a cholesterol ring hydrocarbon framework that is a feature of all steroids.

Steroids and the said compounds may differ structurally in a variety of positions along the cholesterol framework and extending groups. For example, the carbon at position six of the cholesterol ring structure may have a chlorine or methyl group attached. Also, a combination of one or more double bonds may be present within the structure, in particular but not limited to, between carbons four and five, carbons six and seven, carbons eleven and twelve, carbons eleven and twelve, carbons nine and ten, and carbons ten and five. Furthermore, the carbon 17 position (C-17) on the cholesterol ring may have attached an acetyl or a hydroxyl group and also a unique R-group. For example, progesterone has an acetyl group at its C-17 position, whereas 17-OHPC has which the same acetyl group at its C-17 position, also differs with a carboxyl group esterfied at the C-17 position along with a four carbon hydrocarbon chain extending from the same (See chemical structures below). Other synthetic progesterones, such as 17alpha-hydroxyprogesteroneacetate and 17alpha-hydroxyprogesteronevalproate may share similar biological activities as 17-OHPC based on their similar structure. The same may apply to other synthetic progesterones having the same 17-OHPC base structure but possessing different variations of the hydrocarbon chain attached to the carboxyl group present on the C-17 position.

Progesterone

17α-hydroxyprogesterone caproate
(17-OHPC)

Oral micronized progesterone has been reported to have a bioavailability half-life of 16-18 hours. Rathore A. M., et al., Hormones in Obstetrics and Gynaecology. 2015 Jaypee Brothers Publishers. Also, a half-life for progesterone of 12 hours was reported for intramuscular injection and 30 hours via transdermal route. Scott-Moncrieff J. C., et al., Am J Vet Res. 1990 June; 51(6):893-5; Garfield R. E., et al. FVV in OBGYN, 2012, 4(4):237-244. However, synthetic progestogens have a longer half-life than progesterone. Schindler A. E., et al., Maturitas. 2003 Dec. 10; 46 Suppl 1:S7-S16. The half-life of 17-OHPC, a synthetic progestogen, has an apparent half-life of 10 days via injection. Caritis S. N., et al., Am J Obstet Gynecol. 2011 July; 205(1): 40. As for the metabolism of 17-OHPC, it has been reported that the caproate ester is not cleaved and thus 17-OPHC is not broken down to its 17alpha-hydroxyprogestogin form (17-HP). Attardi B. J., et al., Am J Obstet Gynecol. 2007 December; 197(6): 599.e1-599.e7.

As taught by Schindler A. E. et al., progestins "have only one effect in common, the progestogenic effect on the estrogen-primed endometrium of the rabbit, but there are large differences between progestins in the multitude of other biological effects elicited." Supra Schindler A. E. et al. A person with ordinary skill in the art would recognize that P4 and 17-OHPC do not possess the same chemical, biological and pharmacologic effects, and thus, "their synonymous use is inaccurate and misleading". Romero R., et al., Am. J. Obstet. Gynecol. 2013, 208(6): 421-426. Also, referring to progesterone and synthetic progestogens, Dalton K. exemplifies that they "both are valuable drugs with specific indications for their use", noting that "progestogens cannot mimic [the] actions of progesterone". Dalton K., Br Med J 1976, 2:1257.

For example, P4 has been shown to stimulate myometrial contractility, while 17-OHPC has the opposite effect of stimulating myometrial contractility. Ruddock N. K., et al., Am J Obstet Gynecol. 2008, 199: 391. Also, studies by Kuon R. J. et al. demonstrated that P4 may be used to prevent preterm deliveries in women with a short cervix, whereas 17-OHPC does not present the same protective effects. Kuon R. J. et al., Am J Obstet Gynecol. 2010, 202: 455. However, injectable 17-OHPC (Makena®) "is the only drug currently used as a first-line therapy to reduce the risk of preterm birth" in women with a history of preterm birth. Patel Y., et al., PT 201237(7):405-11,405. Also, P4 and 17-OHPC have dissimilar effects on myometrial gene expression. P4 upregulates the expression of defensin-1 in the cervix, whereas 17-OHPC had no detectable effects on gene expression. Nold C., et al., Am J Obstet Gynecol. 2013, 208:223.

P4 also has been shown to increase IL-17 levels resulting in the exacerbation of IL-17 mediated diseases. In short, prior teachings of the P4 genus does not include any predictive therapeutic effects of 17-OHPC, especially with regards to 17-OHPC on IL-17 levels and p38 MAPK activity.

In order to assess the 17-OPHC effects on IL-17 levels in BALF and blood/serum and p38 MAPK activity in the lungs, the inventor has conducted studies on a mouse model system for COPD. It is well known to a person of ordinary skill in the art that results obtained from modeling COPD in mice is an important and necessary step for human studies of the disease. Vlahos R., et al., Clin. Sci. (Loud) 2014 February; 126 (4):253-265. Some of the human conditions of COPD that can be modeled in mice include, but are not limited to BALF/lung inflammation including neutrophilia, accumulation of macrophages and T-cells, and an increase in BALF/lung inflammatory mediators including cytokines, chemokines, and proteases; increased oxidative stress; emphysema; small airway and vascular remodeling; pulmonary hypertension; mucus hypersecretion; impaired lung function; systemic co-morbidities; increased BALF/lung inflammation in response to respiratory pathogens associated with infectious exacerbations; and persistence of BALF/lung inflammation following smoking cessation. Id.

In one exemplary study, sixty (n=60) wild type pathogen-free ten-week old male C57BL/6 mice were acclimatized for one week at room temperature (19-23° C.), 55%±10% humidity, and fed a standard diet. Following acclimatization, mice were exposed to ozone (O3) using an ozoniser. Control animals (n=10 mice, CON group) received medical air only over the equivalent period and administered 0.9% saline in lieu of drug treatment. The ozone exposed mice were subjected to O3 exposure twice a week for three hours at a concentration of 2.5 parts per million (ppm) in a sealed Perspex container for 6 weeks. After the six weeks of O3 exposure, ozone exposure was discontinued in 10 mice (O3 group), and the remaining fifty mice were randomly assigned to the five treatment groups (10 mice/group) with or without inhalation involving 17-OHPC and Budesonide (BUD). Aerosolization of BUD, 17-OHPC, or a combination thereof, was generated by a sidestream jet nebulizer (PARI BOY, Model 37.00, Starnberg, Germany) into the container. Mice were put into stainless cages inside the container with irradiated food and acidified water provided ad libitum. The nebulizer produces a pressure of 1.4-1.5 bar and an airflow of 20 L/min. The test drugs were delivered with the nebulizer at the concentrations described below. Five ml (i.e., total volume) of test drugs were given over 30 minutes for each treatment group. The study drugs were given daily with concurrent ozone exposure. 17-OHPC was administered 12-hours before ozone exposure, while BUD was administered 30 minutes before ozone exposure. 17-OHPC was solubilized in 1% DMSO before the generation of aerosols. Ozone exposure for the treatment groups continued at 2.5 ppm, for 3 hours, twice a week for 10 weeks. The treatment groups are shown and summarized in table 1 below:

TABLE 1

Treatment group conditions

| Treatment Group | O3 | 17-OHPC (mg/L) | BUD (0.2 g/L) |
|---|---|---|---|
| Control (0.9% saline) | − | — | − |
| O3 | + | — | − |
| O3 + 17-OHPC (lo) | + | 0.03 | − |
| O3 + 17-OHPC (hi) | + | 0.3 | − |
| O3 + BUD | + | — | + |
| O3 + BUD + 17-OHPC (lo) | + | 0.03 | + |
| O3 + BUD + 17-OHPC (hi) | + | 0.3 | + |

At the end of 10-week treatments, mice were anesthetized by intraperitoneal injection, and subjected to bronchoalveolar lavage (BAL) for BALF collection as well as venous blood/serum sample collection. The lungs were then extracted with tracheal cannulation. The right lungs were fixed with formalin for 24 hours for histological examinations, and the left lungs were snap-frozen in liquid nitrogen. Using sterile saline in isolating BALE, recovery was more than 80% of eligible specimens. Samples were centrifuged. Cells were washed with Hank's Balanced Saline Solution (HBSS) and counted. Supernatant was measured by enzyme-linked immunosorbent assay (ELISA) for cytokine IL-17 levels in both BALF and serum. Fasting blood was obtained after the specimens were sacrificed. Supernatant was analyzed by ELISA for cytokine IL-17 levels. IL-17 concentration was measured in lung homogenate supernatants using a commercially available IL-17 quantification ELISA kit (R&D Systems) and was performed according to manufacturer's instructions.

Table 2 shows the mean cytokine IL-17 levels in BALF and blood serum from the treatment groups listed above. See also FIG. 1.

TABLE 2

IL-17 levels in BALF and Serum post-drug treatment

| Treatment Group | Cytokine IL-17 (ng/mL) in BALF (Mean ± SD) | Cytokine IL-17 (ng/mL in Serum (Mean ± SD) |
|---|---|---|
| CON | 6.68 ± 2.75 | 33.89 ± 16.00 |
| O3 | 37.09 ± 12.85 | 183.16 ± 52.38 |
| O3 + 17-OHPC (lo) | 27.83 ± 6.72 | 136.17 ± 74.81 |
| O3 + 17-OHPC (hi) | 22.34 ± 13.05 | 104.65 ± 49.04 |
| O3 + BUD | 21.85 ± 8.02 | 126.86 ± 73.82 |
| O3 + BUD + 17-OHPC (lo) | 18.05 ± 9.94 | 88.10 ± 46.31 |
| O3 + BUD + 17-OHPC (hi) | 10.62 ± 2.43 | 67.02 ± 36.57 |

Figure 1:
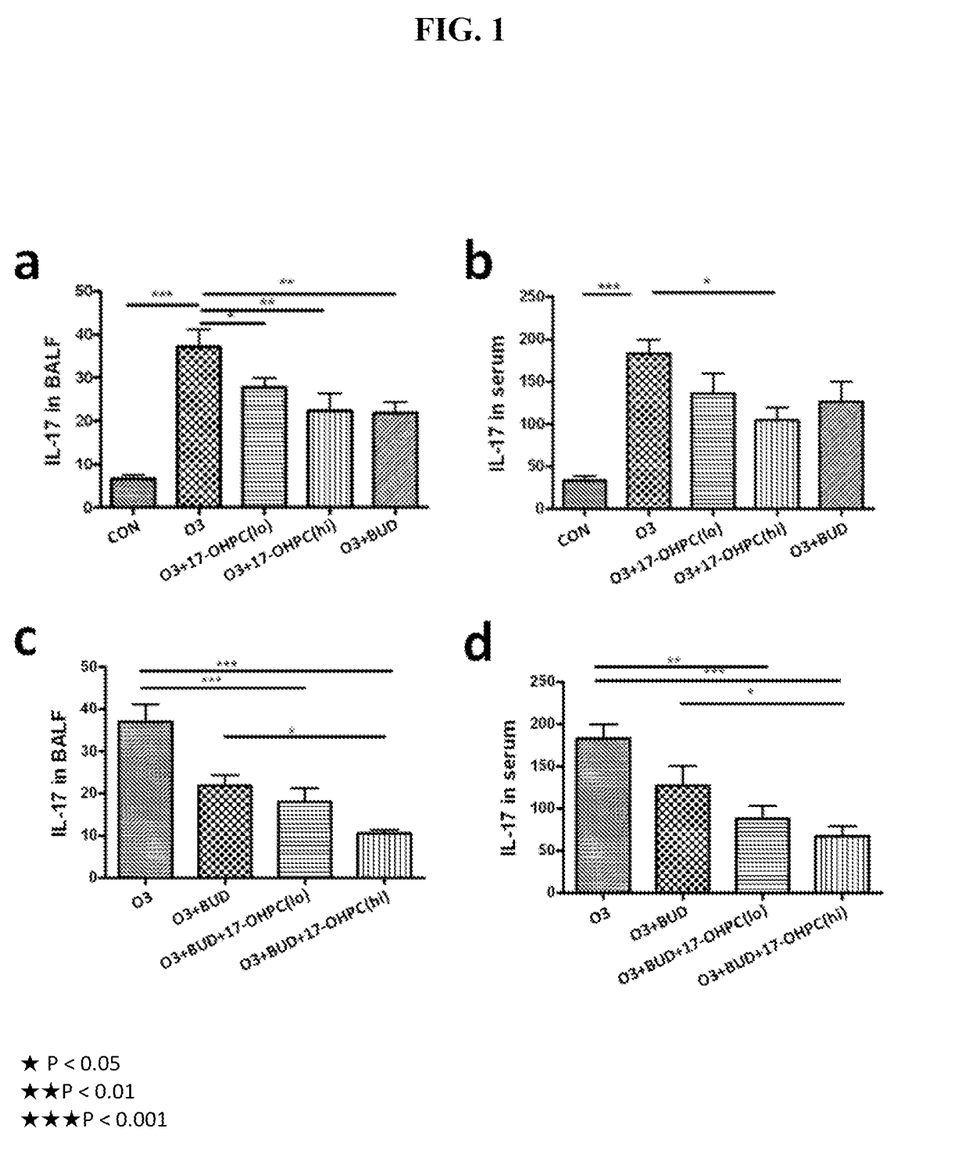
FIG. 1 is a graphical depiction of the IL-17 levels in BALF and in blood serum.

These exemplary studies demonstrate that 17-OPHC has a dramatic effect in lowering IL-17 levels in both BALF and serum. Also, increasing doses of 17-OHPC results in a corresponding reduction of IL-17. IL-17 levels gradually return to within the range of the control mean values under the combined treatment of 17-OPHC and BUD.

In measuring p38 MAPK activity, an exemplary study involves lung tissue from the treatment groups which were extracted and immunoprecipitated from each of the samples and applied to Western blots using primary antibodies for measuring expression of levels of phospho-p38 MAPK and p38 MAPK. Binding of the primary antibody was detected by infrared dye-conjugated secondary antibodies and Odyssey system (Li-Cor, USA), and the bands were quantified with densitometry. The antibodies used to perform immunoprecipitation and Western blots were as follows: mouse anti-p38 MAPK, mouse anti-phospho-p38 phospho-p38 MAPK (Cell Signaling Technology, Mass., US), and mouse anti-α-actin (Sigma Aldrich, St. Louis, Mo.). Ratios of the phospho-p38 MAPK to p38 MAPK are indicated in table 3 and shown in FIG. 2.

TABLE 3 p38MAPK in Lung Tissue

| Treatment Group | Ratio of phospho-p38/p38 |
|---|---|
| CON | 0.47 ± 0.10 |
| O3 | 0.99 ± 0.11 |
| O3 + 17-OHPC (lo) | 0.88 ± 0.07 |
| O3 + 17-OHPC (hi) | 0.81 ± 0.11 |
| O3 + BUD | 0.81 ± 0.11 |
| O3 + BUD + 17-OHPC (lo) | 0.71 ± 0.08 |
| O3 + BUD + 17-OHPC (hi) | 0.67 ± 0.08 |

Figure 2:
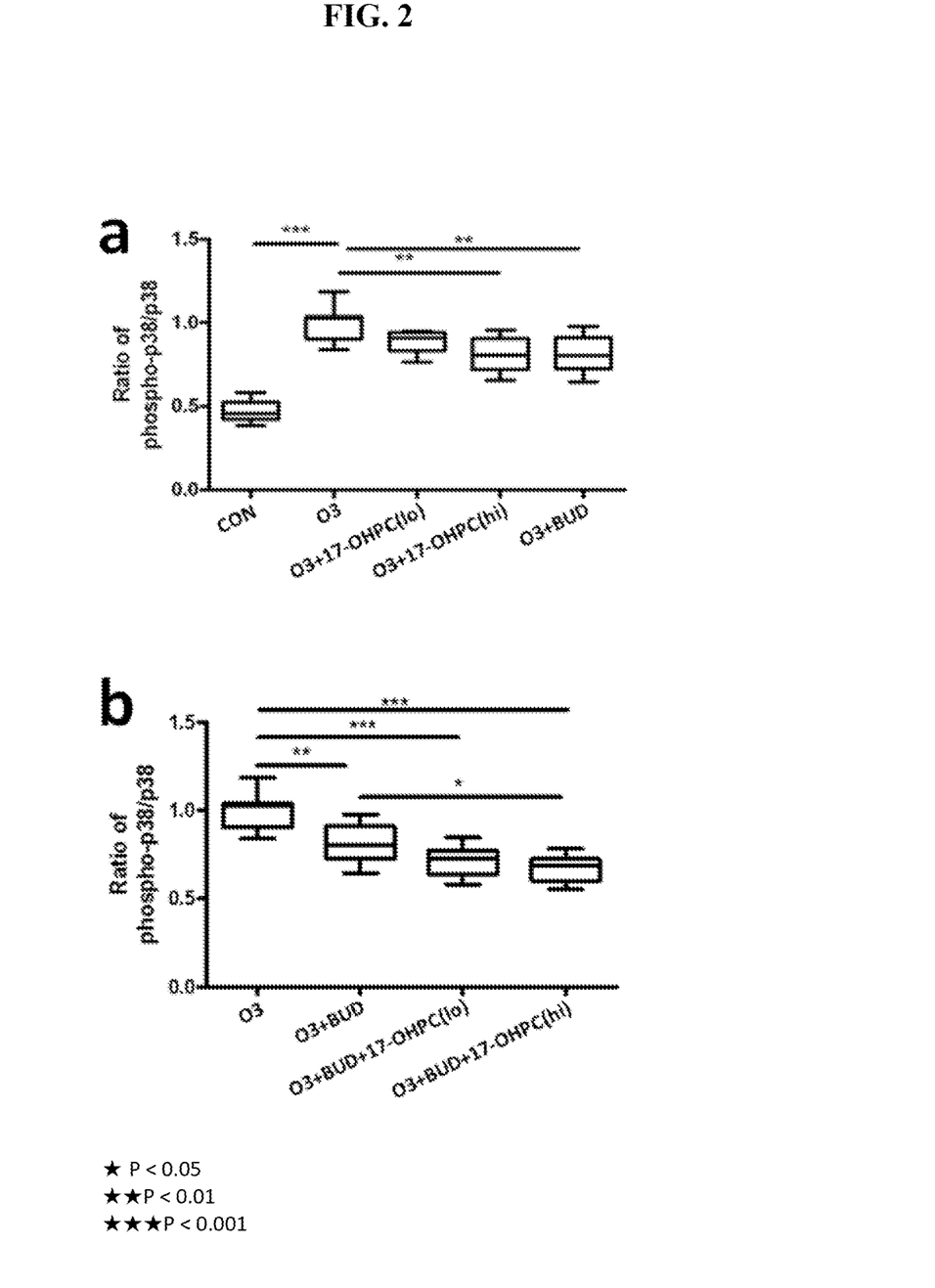
FIG. 2 is a graphical depiction of the ratios of the phospho-p38 MAPK/p38 MAPK in lung tissue.

The Table 3 and FIG. 2 results indicate that under 17-OHPC inhalation treatment, the ratio of phosphorylated to total p38 MAPK (phospho-38/p38) significantly drops with a higher dose of 17-OHPC when compared to a lower 17-OHPC dose. Also, the combined treatment of 17-OHPC and BUD results lower phospho-38/p38 ratio mean values than BUD treatment alone. Thus, these results indicate that the combination of BUD and 17-OHPC may be a preferred treatment than BUD treatment alone for inhibiting p38 activity mediated diseases.

IL-17A and GR Protein Expression in Lung Tissue.
In one exemplary study,

GR and IL-17 protein levels were detected in lung tissue samples collected from the treatment groups. Detection was performed by Western blot analysis of lung tissue from the treatment groups. Nuclear and cytosolic proteins were extracted by using extraction kits from Beyotime, China. Isolated proteins were separated by sodium dodecyl sulfate polyacrylamide gel electrophoresis (SDS-PAGE), transferred onto a polyvinylidene difluoride (PVDF) membrane, and incubated with primary antibodies. Membranes were then incubated with secondary antibodies conjugated with horseradish peroxidase and visualized using enhanced chemiluminescence (ECL) kit. The GR bands and IL-17 protein intensities were adjusted with reference to glyceraldehyde 3-phosphate dehydrogenase (GAPDH) control intensities. The ratios of GR protein to actin and IL-17 to actin are shown in Table 4 and FIG. 3 and FIG. 4.

TABLE 4

GR and IL-17 protein levels in lung tissue

| Treatment Group | GR | IL-17A |
|---|---|---|
| CON | 0.40 ± 0.14 | 0.18 ± 0.10 |
| O3 | 0.24 ± 0.06 | 0.40 ± 0.11 |
| O3 + 17-OHPC (lo) | 0.36 ± 0.10 | 0.35 ± 0.10 |
| O3 + 17-OHPC (hi) | 0.39 ± 0.11 | 0.31 ± 0.085 |
| O3 + BUD | 0.37 ± 0.11 | 0.33 ± 0.07 |
| O3 + BUD + 17-OHPC (lo) | 0.43 ± 0.11 | 0.23 ± 0.08 |
| O3 + BUD + 17-OHPC (hi) | 0.41 ± 0.12 | 0.21 ± 0.07 |

GR is an essential co-factor for the anti-inflammatory efficacy of corticosteroids. GR expression was significantly lower in animals exposed to oxidative stress/stimulation and in patients with COPD than in controls which lead to increased transcription of pro-inflammatory genes associated with a resultant amplification of inflammation and thus corticosteroid insensitivity. As shown in Table 4 and FIG. 3, the observed corticosteroid insensitivity in this O3-induced inflammatory mouse model is consistent with previous studies reported in the literature such that mouse model study shows that GR is an essential co-factor for the anti-inflammatory efficacy of corticosteroids. O3 induced oxidative stress significantly suppresses GR protein expression (vs. control, $P<0.01$).

Figure 3:
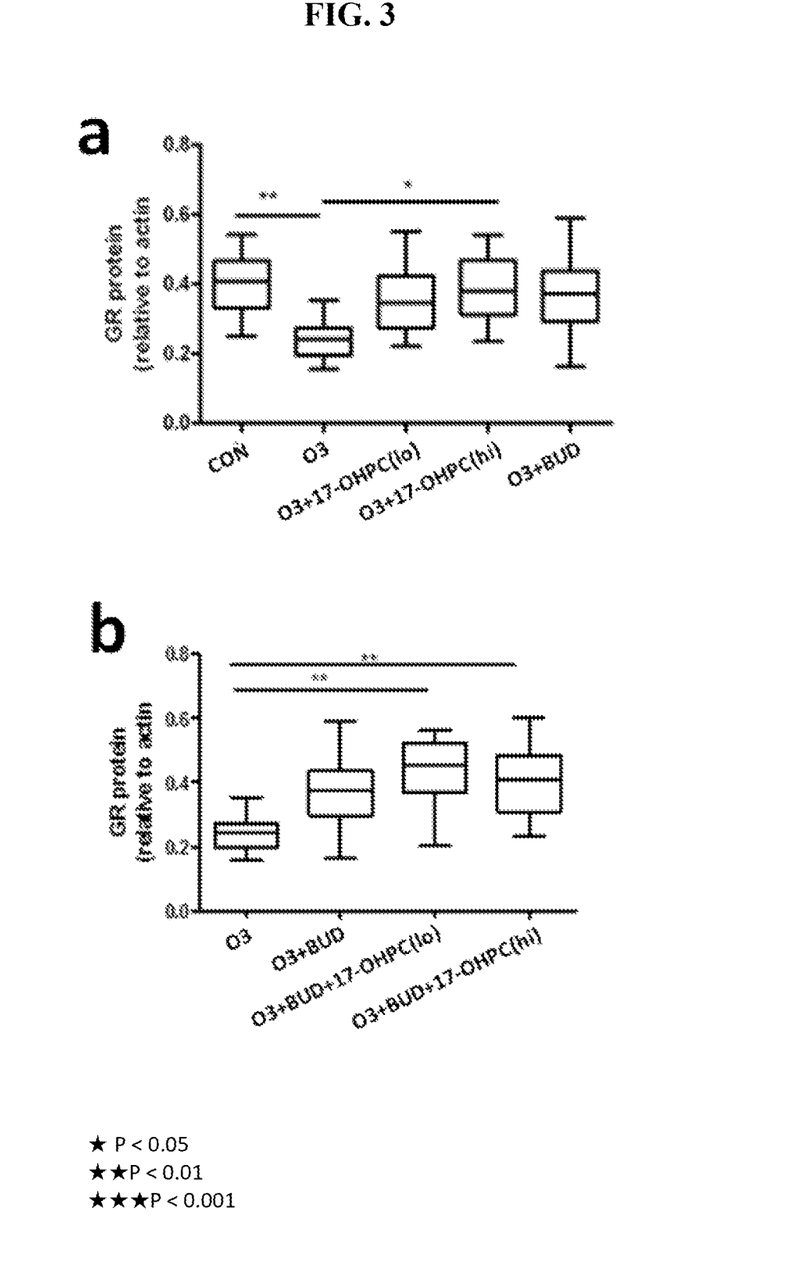
FIG. 3 is a graphical depiction of the ratios of GR protein expression relative to actin in lung tissue of treatment groups.

In this exemplary study, the treatment with 17-OHPC with or without BUD markedly restored O3-reduced GR protein levels ($P<0.05$). In contrast, there were no significant differences on GR protein levels between BUD treatment alone group and O3-exposed group ($P>0.05$), indicating that BUD failed to restore the CS-impaired protein expression of GR. Thus, these results demonstrate that treatment with 17-OHPC or the combination of 17-OHPC and BUD further attenuated O3-induced down-regulation of GR compared with no treatment.

Figure 4:
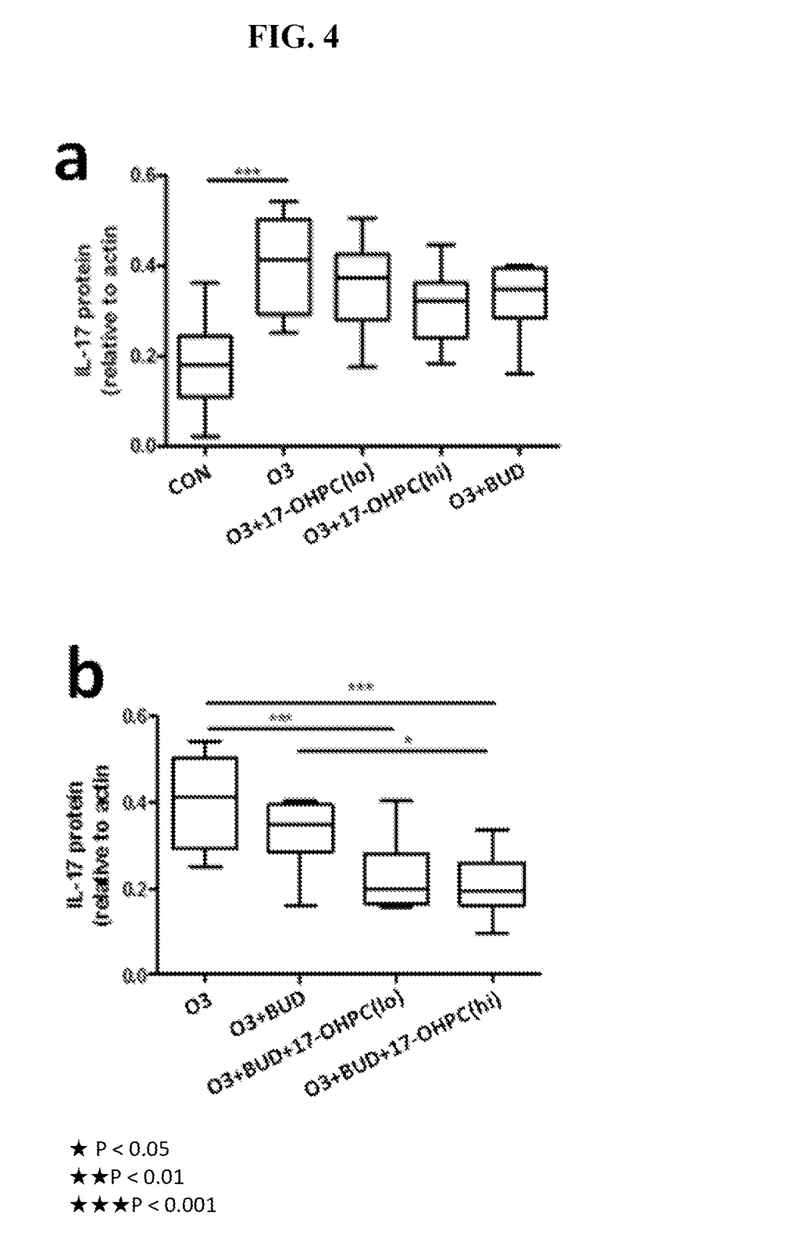
FIG. 4 is a graphical depiction of the ratios of IL-17 protein expression relative to actin in lung tissue of treatment groups.

As shown in Table 4 and FIG. 4, O3 induced oxidative stress significantly increased IL-17 protein expression. Treatment with 17-OHPC lowered ozone-induced IL-17 protein levels compared to the O3 only group. A similar decrease in IL-17 expression was observed in the BUD only treatment group, indicating that BUD failed to fully reduce ozone induced expression of IL-17. However, a combination treatment of BUD and 17-OHPC lowered IL-17 protein expression to near control levels. Thus, 17-OHPC administration as well as its combination with BUD significantly inhibit O3-reduced IL-17 protein levels, and subsequently attenuate O3-induced respiratory inflammatory response.

These results demonstrate that a combination treatment with BUD and 17-OHPC restores O3-reduced GR protein expression and improves glucocorticoid sensitivity than with treatment with BUD or 17-OHPC alone.

Lung Structure and Emphysema.

In another exemplary study, treatment using the present invention demonstrates physiological indicators consistent with the benefits of the treatment. The measure of interalveolar septal wall distance or mean linear intercept (Lm) is common means to evaluate lung structure destruction. Janssens J. P., et al., Eur. Respire. J. 1999; 13:197-205. In one exemplary study, the Lm was determined for each treatment group using a reticule with a Thurlbeck grid comprising of 5 lines (each 550 mM long), with 10 fields per section assessed at random. Lm values are calculated by dividing the length of the line by the number of alveolar wall and grid line interceptions. Results for Lm values for the treatment groups are presented in table 5 and shown in FIG. 5.

TABLE 5

Lung structure analysis

| Treatment Group | Mean Linear Intercept (μm) (Mean ± SD) |
|---|---|
| CON | 78.91 ± 8.54 |
| O3 | 173.9 ± 63.7 |
| O3 + 17-OHPC (lo) | 142.9 ± 45.32 |
| O3 + 17-OHPC (hi) | 137.3 ± 59.3 |
| O3 + BUD | 121.8 ± 38.59 |
| O3 + BUD + 17-OHPC (lo) | 107.1 ± 21.61 |
| O3 + BUD + 17-OHPC (hi) | 92.21 ± 17.99 |

Figure 5:
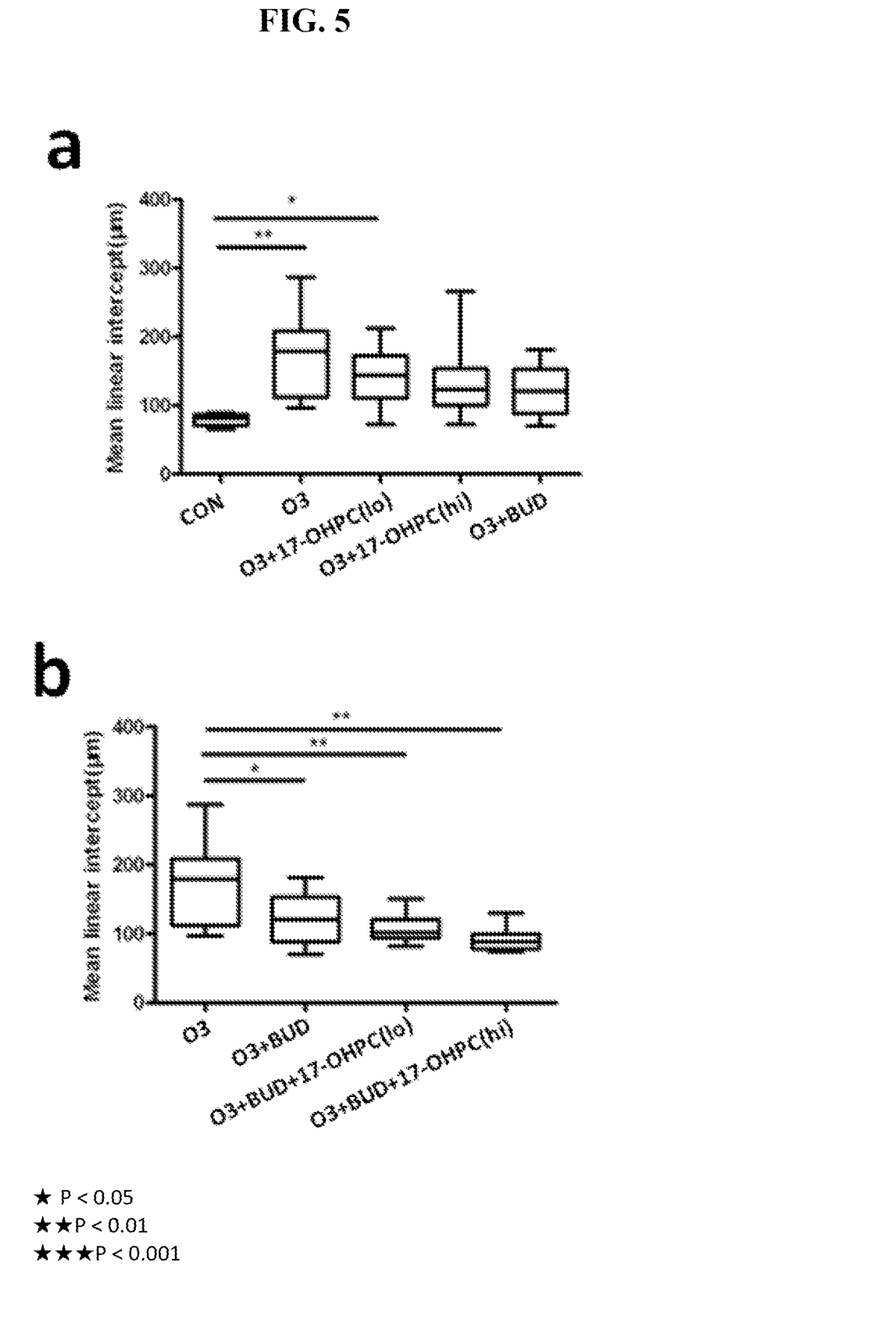
FIG. 5 is a graphical depiction of lung structure of treatment groups.

There is significant difference in Lm in air-exposed C57/BL6 mice between control and O3-exposed group (Table 5 and FIG. 5). Lm was increased in O3-exposed mice compared with air-exposed mice (FIG. 5a), indicating that O3-exposed mice showed an increase in alveolar size and therefore developed an emphysematous-like pattern (ozone: 173.9±63.7 vs. control: 78.91±8.54, P<0.01). Active treatments with BUD and/or 17-OHPC reduce the emphysematous-like change in Lm, and those improvements are statistically significant in BUD, BUD+17-OHPC (lo), and BUD+17-OHPC (hi) groups (vs. O3 only). The treatment group with BUD+17-OHPC showed the best reversion to Lm values comparable to the control group. These results show that 17-OHPC and the combination of 17-OHPC and BUD, can prevent and alleviate alveolar destruction, prevent and alleviate emphysema development, as well as potentially slow down the progression of COPD.

Lung Function.

In another exemplary study, forced maneuver techniques were used to assess lung function parameters. At the end of the study, mice were anesthetized with intraperitoneal injection of ketamine (100 mg/kg) and xylazine (5 mg/kg), and the tracheas were cannulated while maintaining spontaneous breathing. Forced vital capacity (FVC) and the forced expiratory volume (FEV) in the first 25 milliseconds of exhalation were recorded ($FEV_{25}$). The results for $FEV_{25}$ values for the treatment groups are presented in Table 6 and shown in FIG. 6.

TABLE 6

Lung function

| Treatment Group | $FEV_{25}$ |
|---|---|
| CON | 0.38 ± 0.03 |
| O3 | 0.25 ± 0.05 |

TABLE 6-continued

Lung function

| Treatment Group | $FEV_{25}$ |
|---|---|
| O3 + 17-OHPC (lo) | 0.29 ± 0.03 |
| O3 + 17-OHPC (hi) | 0.28 ± 0.03 |
| O3 + BUD | 0.31 ± 0.05 |
| O3 + BUD + 17-OHPC (lo) | 0.33 ± 0.05 |
| O3 + BUD + 17-OHPC (hi) | 0.35 ± 0.05 |

Figure 6:
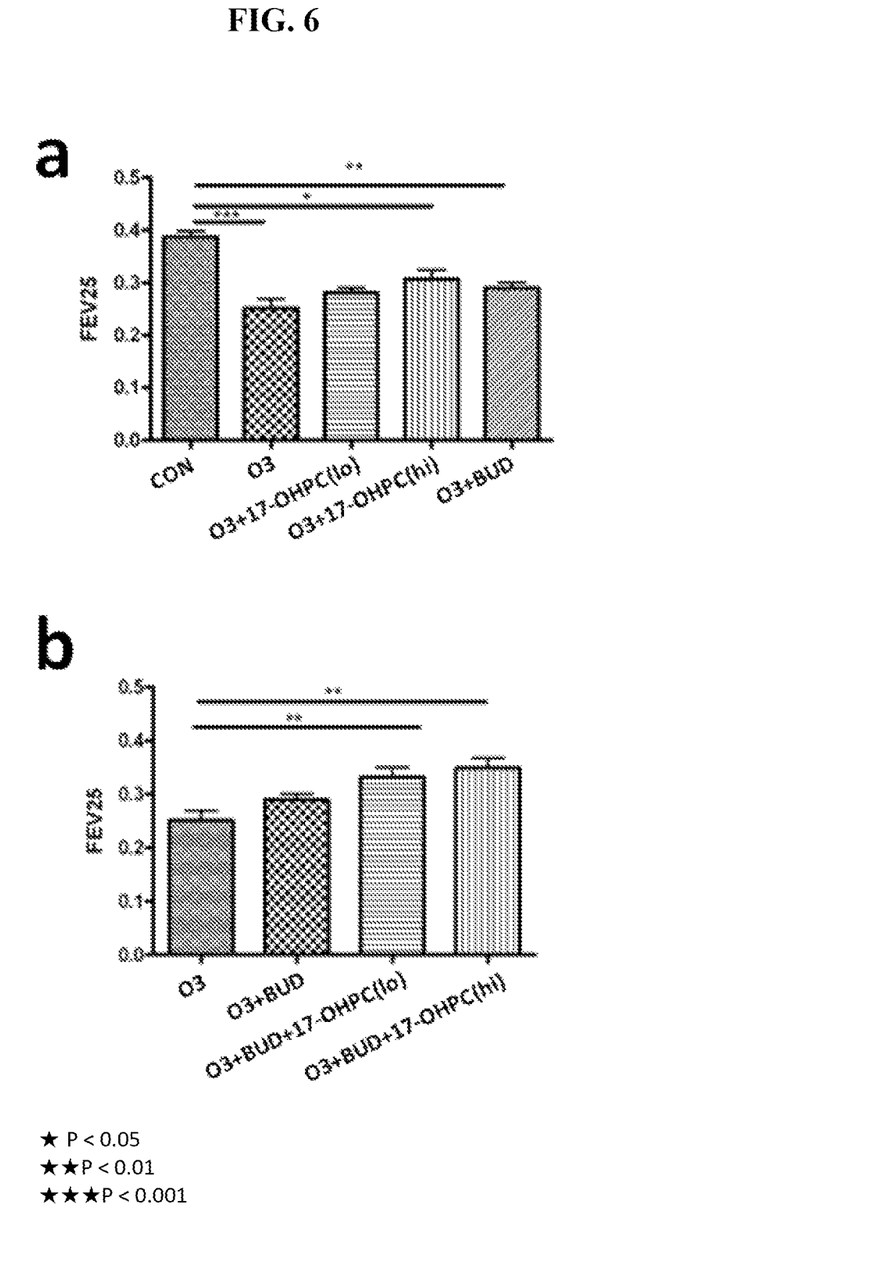
FIG. 6 is a graphical depiction of lung function of treatment groups.

The treatment group with a combination of BUD+17-OHPC significantly improved lung function ($FEV_{25}$) when compared to the O3 group without drug treatment. $FEV_{25}$ values of 0.33±0.05 and 0.35±0.05 were observed for BUD+17-OHPC (lo) and BUD+17-OHPC (hi), respectively; almost completely restoring $FEV_{25}$ to 0.38±0.03 as observed in the control. The BUD+17-OHPC treatment groups showed higher $FEV_{25}$ values, and thus better lung function improvement, than treatment with BUD or 17-OHPC alone.

Inflammation due to O3 exposure results in a limitation of air flow and thus lung function as observed in this study by a reduction of $FEV_{25}$ in the O3 treatment group when compared to the control group. The combination of BUD+17-OHPC treatments significantly improved lung function indicative of the increased $FEV_{25}$ values to near that of the control.

Results similar to the $FEV_{25}$ values were also obtained through measuring the $FEV_{50}$ and $FEV_{100}$.

The results shown herein demonstrate that 17-OHPC and a combination of 17-OHPC and BUD can be used to treat and reduce ozone-induced lung injury, lung inflammation, and oxidative stress on the pulmonary system.

The exemplary study shows that the 17-OHPC may be used as a drug to inhibit IL-17 levels and p38 MAPK activity. 17-OPHC may be used in combination with BUD or any other GC with equivalent properties. This method of treatment may be used to treat IL-17 and/or p38 MAPK mediated auto-immune and auto-inflammatory diseases as earlier mentioned.

It is preferred that a pharmaceutically acceptable composition for inhalation delivery include dry powders comprising an active ingredient present in a dry bulking powder suitable for dry powder inhalation or suspensions suitable for nebulization, and aerosol propellants suitable for use in a metered dose inhaler. Possible formulations may include those describe in the parent patent application Ser. No. 13/021,950. The disclosure of the parent patent application Ser. No. 13/021,950 is incorporated by reference in its entirety herein this reference.

Other routes of delivery may be used for administering effective amounts of 17-OHPC or combinations of 17-OHPC with other medications. Such routes may include parenteral, oral, intravenous delivery, or for local or topical application.

Dosing of the 17-OHPC with or without an added GC may be preferably administered at an interval exceeding daily or once per week. Other dosing regiments may follow the methods disclosed in the parent patent application Ser. No. 13/174,939.

While the specification describes particular embodiments of the present invention, those of ordinary skill in the art can devise variations of the present invention without departing from the inventive concept.

We claim:

1. A method for treating a disease selected from chronic obstructive pulmonary disease, oliterative bronchitis, or asthma with symptoms of reduced airflow to lungs due to smooth muscle hypercontractility and airway remodeling of a patient, said method comprising administering to said patient by inhalation a pharmaceutical composition comprising a first treatment agent comprising 17alpha-hydroxyprogesterone caproate ("17-OHPC") in an amount of from 0.03 mg/L to 0.3 mg/L, a second treatment agent comprising budesonide ("BUD") at 0.2 g/L, and a pharmaceutically acceptable carrier, wherein the disease is mediated by interleukin-17 ("IL-17") and an IL-17 level is reduced in said patient after administration of the pharmaceutical composition compared to an IL-17 level in a patient having the disease and without administration of the pharmaceutical composition.

2. The method of claim 1, wherein said disease comprises symptoms of glucocorticoid insensitivity.

3. The method of claim 1, wherein the 17-OHPC is administered according to a dosing regimen selected from the group of an administration interval less than once per week, once weekly, or exceeding once per week.

4. The method of claim 1, wherein said pharmaceutical composition is administered according to a dosing regimen selected from the group of an administration interval less than once per week, once weekly, or exceeding once per week.

5. A method for reducing IL-17 expression in a patient affected by a disease selected from chronic obstructive pulmonary disease, oliterative bronchitis, or asthma, comprising administering to said patient by inhalation a pharmaceutical composition comprising a first treatment agent comprising 17-OHPC in an amount of from 0.03 mg/L to 0.3 mg/L and a second treatment agent comprising BUD at 0.2 g/L.

6. The method of claim 5, wherein the patient is affected by a condition comprising symptoms of glucocorticoid insensitivity that is associated with said disease.

7. The method of claim 5, wherein the pharmaceutical composition further comprises 17alpha-hydroxyprogesterone acetate or 17-alpha hydroxyprogesterone valproate.

8. A method of treating a respiratory inflammatory disease selected from chronic obstructive pulmonary disease, oliterative bronchitis, or asthma that is mediated by IL-17 in a subject, wherein the respiratory inflammatory disease is characterized by a detectable clinical symptom or change in level of a biochemical marker with respect to the normal range of the marker, the method comprising:
 administering to the subject by inhalation a pharmaceutical composition comprising a first treatment agent comprising 17-OHPC in an amount of from 0.03 mg/L to 0.3 mg/L and a second treatment agent comprising BUD at 0.2 g/L,
 continuing said administration until there is a return of the marker level to a normal range or a desired change in the clinical symptom,
 where the marker or the clinical symptom comprises:
  a decrease in expression of IL-17 in combination with,
  (a) p38 mitogen activated protein kinase activity,
  (b) lung structure, or
  (c) lung function;
 wherein the decrease in expression of IL-17 is compared to an expression level of IL-17 from a subject without administration of the pharmaceutical composition.

9. The method of claim 8, wherein the second treatment agent is administered before, coincident with, or after administration of the first treatment agent.

10. A method for treating a disease mediated by interleukin-17 ("IL-17") selected from chronic obstructive pulmonary disease, oliterative bronchitis, or asthma in a patient in need thereof comprising administering to said patient by inhalation from 0.03 mg/L to 0.3 mg/L of 17alpha-hydroxyprogesterone caproate ("17-OHPC") and 0.2 g/L budesonide ("BUD"), and wherein said treatment comprises a reduction in IL-17 level in said patient after the treatment.

* * * * *